United States Patent [19]

Fukuhara et al.

[11] Patent Number: 4,946,790
[45] Date of Patent: Aug. 7, 1990

[54] RECOMBINANT PLASMID FOR THE EXPRESSION OF L-PHENYLALANINE AMMONIA-LYASE AND TRANSFORMED STRAIN CARRYING SAME

[75] Inventors: Nobuhiro Fukuhara, Ohmuta; Setsuo Yoshino, Yokohama; Satori Sone, Yokohama; Yoshiyuki Nakajima, Yokohama; Nobuyoshi Makiguchi, Fujisawa, all of Japan

[73] Assignee: Mitsui Toatsu Chemicals, Inc., Tokyo, Japan

[21] Appl. No.: 151,234

[22] Filed: Feb. 1, 1988

[30] Foreign Application Priority Data

Feb. 6, 1987 [JP] Japan .................................. 62-024705
Jun. 18, 1987 [JP] Japan .................................. 62-152357

[51] Int. Cl.$^5$ ......................... C12N 1/21; C12N 15/70
[52] U.S. Cl. ............................... 435/252.33; 435/320; 935/29; 935/73
[58] Field of Search ................. 435/252.33, 320, 172.3; 935/9, 14, 29, 41, 73

[56] References Cited

FOREIGN PATENT DOCUMENTS 0152613 5/1987 European Pat. Off. .
0260919 3/1988 European Pat. Off. .
0279664 8/1988 European Pat. Off. .
WO88/02024 3/1988 PCT Int'l Appl. .

OTHER PUBLICATIONS

Gilbert, H. J.; Clark, I. N.; Gibson, R. K.; Stephenson, J. R.; and Tully, M., "Molecular Cloning of the Phenylalanine Ammonia–Lyase Gene from *Rhodosporidium Toruloides* in *Escherichia Coli* K–12", *Journal of Bacteriology*, Jan. 1985, pp. 314–320.

Anson, J. G.; Gilbert, H. J.; Oram, J. D.; and Minton, N. P., "Complete Nucleotide Sequence of the *Rhodosporidium Toruloides* Gene Coding for Phenylalanine Ammonia–Lyase", *Gene* 58(1987), 189–199.

*Gene*, vol. 58, No. 2–3, 1987, pp. 189–199, Anson et al., "Complete Nucleotide Sequence of the Rhodosporidium toruloides gene . . .".

Primary Examiner—Elizabeth C. Weimar
Assistant Examiner—Marian C. Knode
Attorney, Agent, or Firm—Nixon & Vanderhye

[57] ABSTRACT

A recombinant plasmid for the expression of phenylalanine ammonia-lyase (PAL) is constructed by incorporating therein a combined promoter comprising (a) the fusion promoter (the tac promoter) composed of the trp promoter minus 35 region and the lac UV-5 promoter minus 10 region and (b) the $P_L$ promoter of the lambda phage, the tac promoter and the $P_L$ promoter being connected so as to have the same directional property. This recombinant plasmid permits more efficient expression of PAL in *Escherichia coli*.

3 Claims, 16 Drawing Sheets

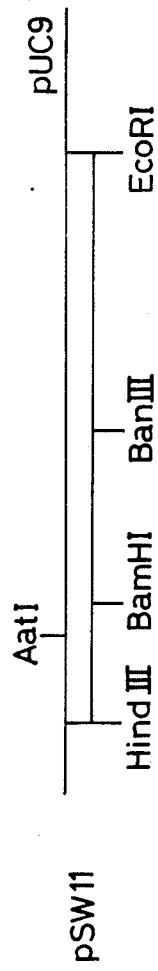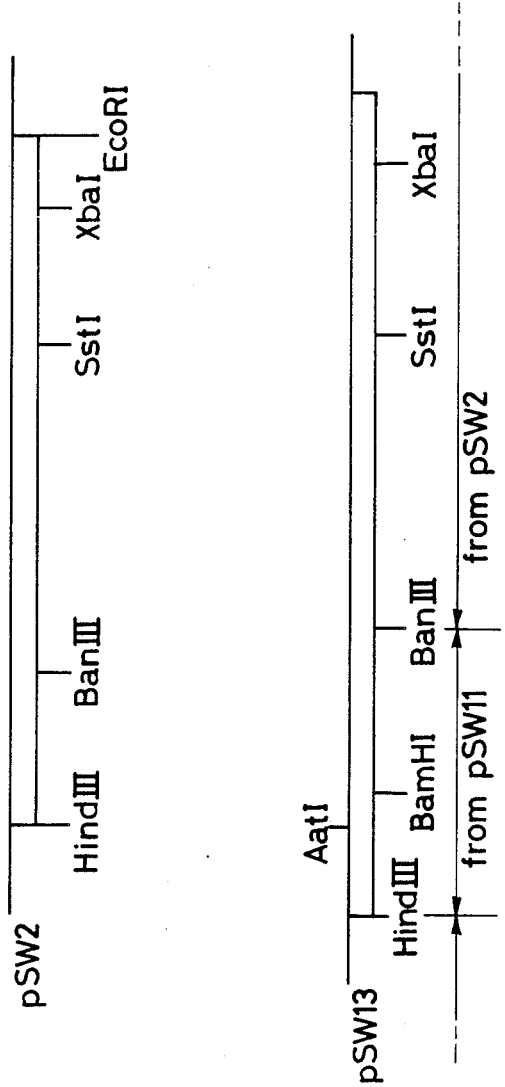
F I G. 1

FIG. 2(A)

```
         10         20         30         40         50         60
ATGGCACCCTCGCTCGACTCGATCTCGCACTCGTTCGCAAACGGGCGTCGCATCCGCAAAG
         70         80         90        100        110        120
CAGGCTGTCAATGGCGCCTCGACCAACCTCGCAGTCGCAGGCTCGCACCTGCCCACAACC
        130        140        150        160        170        180
CAGGTCACGCAGGTCGACATCGTCGAGAAGATGCTCGCGGCCGACTCGACGCTC
        190        200        210        220        230        240
GAACTCGACGGCTACTCGCTCAACCCTCGGAGACGTCGTCTCGGCCGCGAGGAAGGGCAGG
        250        260        270        280        290        300
CCTGTCCGGCGTCAAGGACAGCGACGAGATCCGCTCAAAGATTGACAAATCGGTCGAGTTC
        310        320        330        340        350        360
TTGCGCTCAACTCTCCATGAGCGTCTACGGCGTCACGACTGGATTTGGCGGATCCGCA
        370        380        390        400        410        420
GACACCCGCACCGAGGACGCCATCTCGCTCCAGAAGGCTCTCCTCGAGCACCAGCTCTGC
        430        440        450        460        470        480
GGTGTTCTCCCTTCGTTCGACTCGTTCCGCCTCGGCCCTCGGCCGGTCTCGAGAACTCGCTT
        490        500        510        520        530        540
CCCCTCGAGGTTGTTCGCGGCGCCATGACAATCCGCGTCAACAGCTTGACCCGGCCAC
        550        560        570        580        590        600
TCGGCTGTCCGCCTCGTCGTCCTCGAGGCGCTCACCAACTTCCTCAACGGCATCACC
```

FIG. 2(B)

```
     610       620       630       640       650       660
CCCATCGTCCGCCCTCCGCGGCACCATCTCTGCGTCGGCGACCTCTCTCCTCTCTCCTAC
     670       680       690       700       710       720
ATTGCAGCGGGCCATCAGCGGTCAACCCGGACAGCAAGGTGCACGTCGTCCACGAGGGCAAG
     730       740       750       760       770       780
GAGAAGATCCTGTACGCCCGGCGAGGCGATGGCGCTCTTCAACCTCGAGCCCGTCGTCCTC
     790       800       810       820       830       840
GGCCCGAAGGAAGGTCTCGGTGTCTCGTCAACGGCACCGCGTCTCAGCATCGATGGCCACC
     850       860       870       880       890       900
CTCGGCTCTGCACGACGCACACATGCTCTCGCTCCTCTCGCAGTCGCTCACGGCCATGACG
     910       920       930       940       950       960
GTCGAAGCGATGGTCGGCACGCGCCGGTCGTTCCACCCCTTCCTTCACGACGTCACGCGC
     970       980       990      1000      1010      1020
CCTCACCCGACGCAGATCGAAGTCGCGGAAACATCCGCAAGCTCCTCGAGGGAAGCCGC
    1030      1040      1050      1060      1070      1080
TTTGCTGTCCACCATGAGGAGGAGGTCAAGGTCAAGGACGACGAGGCATTCTCCGCCAG
    1090      1100      1110      1120      1130      1140
GACCGCTACCCCCTTGCGCACGTCTCCTCAGTGGCTCGGCCCGCTCGTCAGCGACCTCATT
    1150      1160      1170      1180      1190      1200
CACGCCCACGCCGTCCTCACCATCGAGGCCGGCCAGTCGACGACCGACGACAACCCTCTCATC
```

FIG. 2(D)

```
              1810      1820      1830      1840      1850      1860
TTCTCCTTCGCCGCCGGCACCGTCGTCGAGGTCCCTCTCGTCGACGTCGCTCTCGCTCGCC
              1870      1880      1890      1900      1910      1920
GCCGTCAACGCCCTGGAAGGTCGCCGCCGAGTCGGCCATCTCGCTCACCCGCCAAGTC
              1930      1940      1950      1960      1970      1980
CGCGAGACCTTCTGGTCCGCCGGCGTCGACCTCGTCGCGCTCTCGTACCTCTCGCCG
              1990      2000      2010      2020      2030      2040
CGCACTCAGATCCTCTACGCCCTTCGTCCGCGAGGAGCTTGGCGTCAAGGCCCGCCGGA
              2050      2060      2070      2080      2090      2100
GACGTCTTCCTCGGCAAGAGGTGACGATCGGCTCGAACGTCTCCAAGATCTACGAG
              2110      2120      2130      2140      2150
GCCATCAAGTCGGGCAGGATCAACAACGTCCTCCTCAAGATGCTCGCTTAGACACTCTTC
CCACTCTCGCATCCCCTTCCATACCCTATCCCGCCTGCACTCTTAGGACTCGGCTTTCTTGTC
GGACTCGGATCTCGCATCGCTTCTTTCGTTCTTGGCTGCCTCTCTAGACCGTGTCGGTAT
TACCTCGAGATTGTGAATACAAGCAGTACCCATCCAAAAAAAAAAAAAAAA
```

FIG.2(C)

```
        1210       1220       1230       1240       1250       1260
GACGTCGAGAACAAGACTTCGCACCACGGCGGGCAATTTCCAGGCTGCCGCTGTGGCCAAC
        1270       1280       1290       1300       1310       1320
ACCATGGAGAAGACTCGCCTCGGGCTCGCCCAGATCGGCAAGCTCAACTTCACGCAGCTC
        1330       1340       1350       1360       1370       1380
ACCGAGATGCTCAACGCCGGGCATGAACGCGGCCTCCCCTCCTGCCTTCGCGGCCGAAGAC
        1390       1400       1410       1420       1430       1440
CCCTCGCTCTCCTACCACTGCAAGGGCCTCGACATCGCCGTGCGGGCGTACACCTCGGAG
        1450       1460       1470       1480       1490       1500
TTGGGACACCTCGCCAACCCTGTGACGACGCATGTCCAGCCGGCTGAGATGGCGAACCAG
        1510       1520       1530       1540       1550       1560
GCGGTCAACTCGCTTGCGCTCATCTCGGCTCGTCGACGACCGAGTCCAACGACGTCCTTT
        1570       1580       1590       1600       1610       1620
TCTCTCCTCGCCACCCTCTACTGCGTTCTCTCCAAGCCATCGCTCGCTTGCGCGCGATC
        1630       1640       1650       1660       1670       1680
GAGTTCGAAGAAGCAGTTCGGCCCAGCCATCGTCTCGCTCATCGACCAGCACTTT
        1690       1700       1710       1720       1730       1740
GGCTCCGCCATGACCGGCTCGAACCTGTCGTCGAGAAGGTGAACAAGACG
        1750       1760       1770       1780       1790       1800
CTCGCCAAGCGCCTCGAGCAGACCAACTCGTACGACCTCGTCCCGGCTCCCGGCACGACGCC
```

4,946,790

RECOMBINANT PLASMID FOR THE EXPRESSION OF L-PHENYLALANINE AMMONIA-LYASE AND TRANSFORMED STRAIN CARRYING SAME

BACKGROUND OF THE INVENTION

1. Field of the Invention

This invention relates to a recombinant plasmid (a hybrid plasmid) permitting efficient expression of L-phenylalanine ammonia-lyase (hereinafter abbreviated as PAL) in *Escherichia coli*, and a strain of *E. coli* which has been transformed with the recombinant plasmid.

More particularly, the invention relates to a hybrid plasmid characterized in that, when the hybrid plasmid is constructed by inserting the structural gene for PAL in an expression vector enabling the expression of an exogenous gene in *E. coli* according to gene manipulation techniques, a combined promoter obtained by connecting, in a specified order, (a) a hybrid promoter (the tac promoter) constructed from the trp promoter minus 35 region and the lac UV-5 promoter minus 10 region with (b) the $P_L$ promoter of the lambda phage, the so constructed tandem promoter is used as the promoter for the expression of the structural gene for PAL. By using the hybrid plasmid, more efficient expression of PAL in *E. coli* can be achieved. This invention further relates to a strain of *E. coli* which has been transformed with the hybrid plasmid.

2. DESCRIPTION OF THE PRIOR ART

PAL is an enzyme catalyzing the reaction in which ammonia is removed from L-phenylalanine to form trans-cinnamic acid. Accordingly, it is useful in the production of L-phenylalanine from cinnamic acid and ammonia by utilizing the reverse reaction.

In the past, PAL has been prepared by extraction from yeasts, molds and plants. However, such organisms that produce PAL can only give a slight yield of PAL, and it has been difficult to prepare PAL on an industrial scale.

Accordingly, as a means for realizing the mass production of PAL, much attention is focused on the genetic recombination technique which enables mass-culturable microorganisms (such as *E. coli* and the like) to produce PAL.

From this point of view, the present inventors have elucidated the construction of the structural gene for PAL derived from *Rhodosporidium toruloides* and have succeeded in causing PAL (i.e., the product of the structural gene) to be expressed in *E. coli*.

Meanwhile, as a host microorganism serving to produce an exogenous protein (i.e., a protein which is not normally produced by the host microorganism) by utilization of the genetic recombination technique, *E. coli* is being widely used because its biological properties have been fully analyzed, it is not pathogenic, and it can be readily cultured in a medium having a simple composition.

As an expression vector allowing the desired protein to be expressed in *E. coli*, the vector used is one which basically comprises a promoter permitting the transcription, in *E. coli*, of a DNA sequence located downstream of the promoter and containing the region coding for the desired exogenous protein, and a vector capable of replicating in *E. coli*.

Various types of promoters are available for use as the promoter incorporated in such an expression vector. For example, the $P_L$ promoter of the lambda phage of *E. coli* (hereinafter referred to as the $P_L$ lambda promoter), the promoter of the tryptophan operon of *E. coli* (hereinafter referred to as the trp promoter), the promoter of the lactose operon of *E. coli* (hereinafter referred to as the lac promoter), and the fusion promoter (hereinafter referred to as the tac promoter) composed of the trp promoter and the lac promoter are being widely used for that purpose.

Moreover, in order to produce exogenous proteins more efficiently by the use of expression vectors, further investigations are required to search for a new, highly active promoter permitting more efficient expression and/or enhance the activity of conventionally known promoters.

For example, K. Mackenney et al. made an attempt to obtain a more active promoter by connecting a plurality of promoters in series [Gene Amplification and Analysis, Vol. II, pp. 383–415, Elsevier Science Publishing Co., New York (1981)]. Moreover, in order to accomplish the same purpose, Japanese Patent Laid-Open No. 126086/'85 discloses tandem promoters constructed by connecting the $P_L$ lambda promoter or the $P_R$ promoter (i.e., the $P_R$ promoter of the lambda phage of *E. coli*) in series with the trp promoter or the lac promoter so that the former is located upstream of the latter.

However, the compatibility of the promoter incorporated in an expression vector with the protein to be expressed thereby has not been fully elucidated yet. Accordingly, it is very difficult to make a theoretical presumption, for example, as to whether or not a promoter having high activity for the expression of some proteins can also exhibit high activity for the expression of other proteins. Moreover, much remains unknown about the action of a tandem promoter used to enhance expression efficiency. Thus, the types of promoters to be connected and the order of connection of them must be determined according to the type of a protein to be expressed.

Accordingly, it is necessary to select or develop a promoter permitting more efficient expression, for each of the proteins to be expressed.

For these reasons, the selection or development of a more suitable promoter for the expression of PAL in *E. coli* has been urgently needed.

Moreover, it has been found that the conventionally known promoters, such as those enumerated above, fail to provide satisfactorily high expression efficiency. Thus, there is a need to develop a new promoter suitable for high-level expression of PAL.

SUMMARY OF THE INVENTION

From the above point of view, the present inventors made an attempt to develop an expression vector suitable for the production of PAL in *E. coli* according to the aforesaid gene manipulation technique, with their attention focused on the combination of the expression level of PAL and the promoter incorporated in the expression vector. Furthermore, by using various combined promoters, the present inventors also made an extensive investigation on the relationship between the arrangement of the constituent promoters and the expression level of PAL. As a result, it has been found that highly efficient expression of PAL in *E. coli* can be achieved by using, as the promoter of the expression vector, a combined promoter comprising the tac promoter and the $P_L$ promoter arranged in a specified direction and order. The present invention has been completed on the basis of this finding.

The object of the present invention is to make improvements in the production of PAL in *E. coli* according to gene manipulation techniques. More specifically, the object of the present invention is to provide a hybrid plasmid which permits more efficient expression of PAL in *E. coli*, as well as a strain of *E. coli* which has been transformed with the plasmid and is suitable for use in the mass production of PAL.

In order to accomplish the above and other objects, the present invention provides (A) a hybrid plasmid having (a) a vector capable of replicating in *E. coli*, (b) a combined promoter comprising the tac promoter (the fusion promoter composed of the trp promoter minus 35 region and the lac UV-5 promoter minus 10 region) and the $P_L$ lambda promoter (the $P_L$ promoter of the lambda phase), the $P_L$ lambda promoter being connected downstream of the tac promoter, and (c) a DNA sequence coding for L-phenylalanine ammonia-lyase, the DNA sequence being inserted downstream of the combined promoter, the recombinant plasmid being further characterized in that the two promoters constituting the combined promoter have the same directional property and in that the $P_L$ promoter is located upstream of the DNA sequence so as to have the directional property which permits transcription of the DNA sequence; as well as (B) a strain of *E. coli* which has been transformed with the plasmid.

The hybrid plasmid of the present invention has the structure in which a combined promoter comprising the tac promoter and the $P_L$ lambda promoter is located upstream of a DNA sequence coding for PAL in a specified positional relationship. This characteristic structure makes it possible to achieve more efficient expression of PAL.

Moreover, a transformed strain useful in the efficient mass production of PAL can be obtained by transforming *E. coli* with the hybrid plasmid of the present invention.

BRIEF DESCRIPTION OF THE DRAWINGS

FIG. 1 shows restriction endonuclease cleavage maps of the portions of pSW11, pSW2 and pSW13 which are concerned with the structural gene for PAL;

FIGS. 2(A) to 2(D) show the nucleotide sequence of one strand of a DNA sequence including the region coding for phenylalanine ammonia-lyase and contained in the structural gene for PAL cloned in Reference Example;

DETAILED DESCRIPTION OF THE INVENTION

Figure 3:
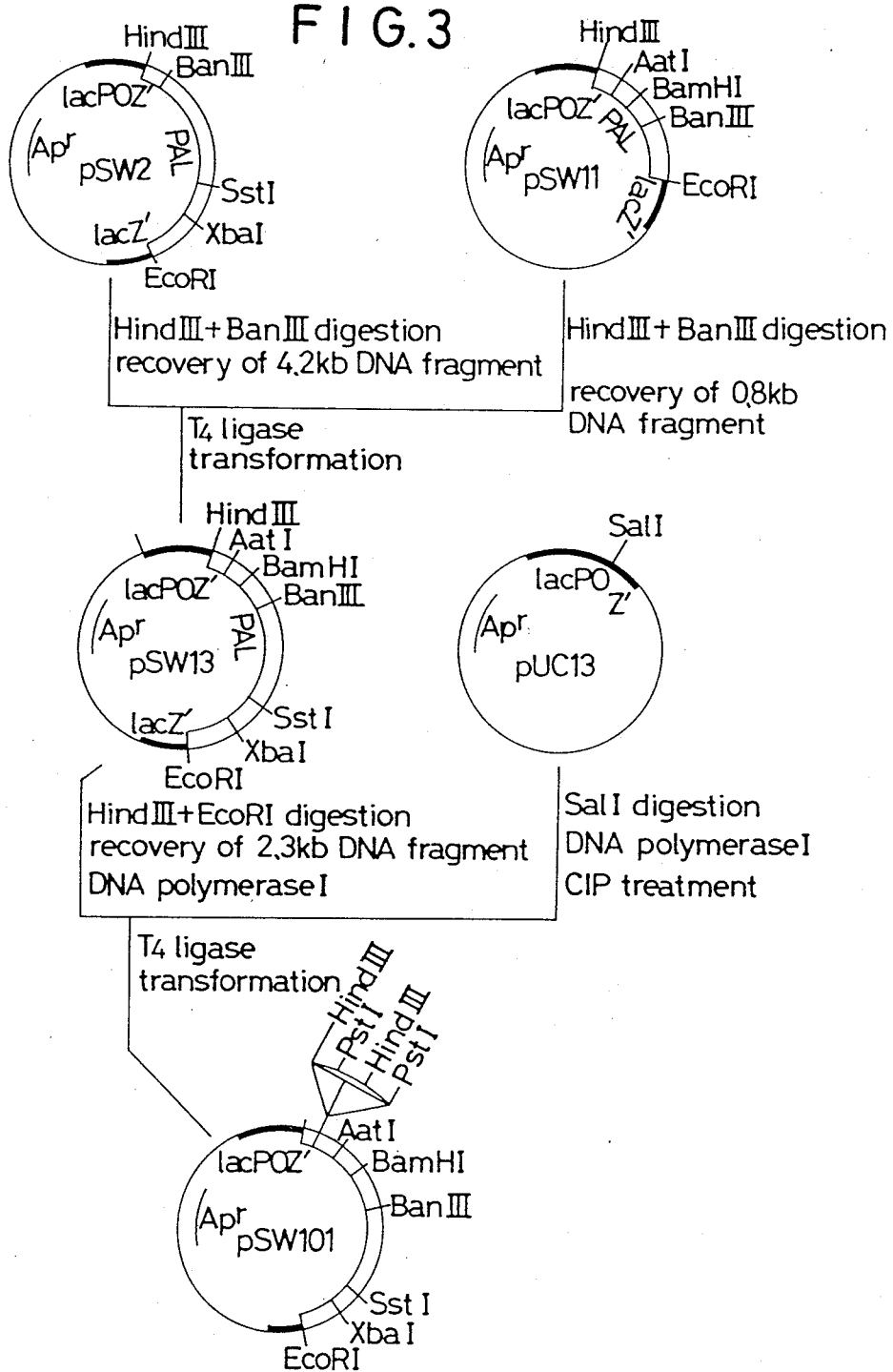
FIG. 3 is a flow chart illustrating the procedure for constructing the plasmid pSW101.

The hybrid plasmid for the expression of PAL in accordance with the present invention is a recombinant plasmid comprising (a) a vector capable of replicating in *E. coli*, (b) a combined promoter comprising the tac promoter which is a fusion promoter composed of the trp promoter minus 35 region and the lac UV-5 promoter minus 10 region, and the P lambda promoter, the $P_L$ lambda promoter being connected downstream of the tac promoter, and (c) a DNA sequence coding for L-phenylalanine ammonialyase, the DNA sequence being inserted downstream of the combined promoter, the recombinant plasmid being further characterized in that the two promoters constituting the combined promoter have the same directional property and in that the $P_L$ promoter is located upstream of the DNA sequence so as to have the directional property which permits transcription of the DNA sequence.

As used herein, the terms "upstream" and "downstream" mean that, when the reference direction is defined as the direction leading from the initiation codon to the termination codon of the DNA sequence coding for PAL, the side of a point lying in the same direction as the reference direction is "downstream" of the point and the side lying in the direction opposite to the reference direction is "upstream" of the point.

The vector used in the hybrid plasmid of the present invention can be any DNA fragment that is stably retained in the *E. coli* and is capable of replicating therein (i.e., has an origin of replication capable of functioning properly in *E. coli*).

As the origin of replication of the vector, there may be used those derived from pMB1, pSC101, ColE1 and p15A. Among others, the origin of replication derived from the plasmid pBR322 is preferred because it originates from pMB1 and can be multicopied in *E. coli*.

Moreover, the aforesaid vector may conveniently contain a gene serving as a selection marker when the hybrid plasmid is introduced into the host microorganism.

As the marker gene, there may be used various genes permitting the expression of ampicillin resistance in *E. coli*, such as those derived from the plasmids pBR322, pKC7, pMK16, pMG411, pACYC184 and the like; various genes permitting the expression of tetracycline resistance, kanamycin resistance or the like; and the lacZ gene.

The combined promoter incorporated in the hybrid plasmid of the present invention comprises the tac promoter (that is a fusion promoter derived from the trp promoter and the lac promoter), and the $P_L$ lambda promoter which is connected downstream of the fusion promoter.

The tac promoter used in this combined promoter can be constructed from the trp promoter minus 35 region and the lac UV-5 promoter minus 10 region according to the method reported by Bennet, G.N., et al., [Gene, 20, 231 (1982)]. Alternatively, the tac promoter used for this purpose may be cut out of suitable vectors containing it, such as the plasmid pKK223-3 (a product of Pharmacia Co.) constructed by J. Birosius et al.

This tac promoter should preferably contain the SD sequence (Shine-Dalgano sequence).

As the $P_L$ lambda promoter, there may be used a segment, that, contained, for example, in a HindIII-BamHI segment of the DNA of the lambda phage for *E. coli*. This segment can be directly cut out of the lambda phage DNA by treatment with the restriction endonucleases HindIII and BamHI. Alternatively, the segment may also be cut out of suitable plasmids containing it, such at that used in the method of Shimatake et al. [*Nature*, 292, 128 (1981)].

When these two promoters constituting the combined promoter are incorporated into the hybrid plasmid, they should be arranged so as to have the same directional relationship, as described previously.

As used herein, the term "same directional property" means that the RNA polymerase recognition site and RNA polymerase binding site characteristic of a promoter are arranged in the same order for both the tac promoter and the $P_L$ lambda promoter.

Moreover, the $P_L$ lambda promoter located downstream of the tac promoter in the combined promoter should be disposed so as to have the directional property which renders it active enough to permit transcription of the DNA sequence located downstream of it (i.e., the directional property in which the RNA polymerase recognition site is located downstream of its RNA polymerase recognition site), and should contain the SD sequence of the $P_L$ promoter.

In the hybrid plasmid of the present invention, the DNA sequence coding for PAL and located downstream of the combined promoter constructed in the above-described manner can be, for example, the DNA sequence (with an initiation codon and a termination codon) containing the structural gene for PAL and having been cloned from a yeast of the genus Rhodosporidium by the present inventors according to the procedure described in the Reference Example given later. Moreover, there may also be used DNA sequences cloned from various types of plants, animals and microorganisms having the ability to produce PAL.

In the hybrid plasmid of the present invention, the mRNA terminator incorporated therein so as to be located downstream of the DNA sequence coding for PAL can be any terminator that functions properly in *E. coli*. However, in order to maintain a balance with the activity of the aforesaid combined promoter, it is desirable to use a terminator (such as rrnB, trpA or the like) having powerful activity.

The hybrid plasmid of the present invention can be constructed by connecting the aforesaid constituents in the above-defined order according to genetic recombination techniques.

As the methods for connecting the aforesaid constituents, there may be used, for example, those developed by the present inventors and described in the Example given later.

In the hybrid plasmid constructed in the above-described manner, the aforesaid marker gene and origin of replication are preferably connected in such a way that they are arranged in that order and located downstream of the terminator connected downstream of the DNA sequence coding for PAL and that each of them has the directional property permitting it to function properly from the upstream to the downstream side.

When the hybrid plasmid of the present invention which has been constructed in the above-described manner is introduced into the *E. coli* host, it becomes possible to achieve more efficient expression of PAL in the *E. coli* host.

The present invention will be more specifically explained with reference to the following Reference Example, Example and Comparative Examples.

(REFERENCE EXAMPLE)

A procedure for cloning the structural gene for PAL is described hereinbelow as a reference example.

REFERENCE EXAMPLE

1. Isolation and Purification of the mRNA for PAL

Using a synthetic medium (Table 1) containing 2% glucose, *Rhodosporidium toruloides* IFO 559 (also identified as ATCC 10788) was grown at 27° C. under aerated and agitated conditions. Immediately after all of the glucose added at the beginning of the culture was consumed, the cells were collected by centrifugation. The collected wet cells were washed with 0.85% sterile saline and collected again by centrifugation to obtain wet washed cells.

TABLE 1

| Glucose | 20 | g/l | Biotin | 2 μg/l |
|---|---|---|---|---|
| $(NH_4)_2SO_4$ | 3 | " | Calcium pantothenate | 400 |
| $KH_2PH_4$ | 1 | " | Inositol | 2000 |
| $MgSO_4.7H_2O$ | 0.5 | " | Niacin | 400 |
| NaCl | 0.1 | " | p-Aminobenzoic acid | 200 |
| $CaCl_2$ | 0.1 | " | Pyridoxine hydrochloride | 400 |
| | | | Riboflavin | 200 |
| | | | Thiamine hydrochloride | 400 |

These wet washed cells were immediately suspended in a PAL induction medium [i.e., 0.17% Yeast Nitrogen Base (a product of Difco; ammonium sulfate-free and amino acid-free type) containing 2% L-Phe] in a cell concentration of 0.5–0.8%, and the resulting suspension was shaken at 27° C. to induce PAL.

After 2 hours' PAL induction treatment at 27° C., the cells were recovered from the PAL induction medium by centrifugation. The collected wet cells were suspended in an equal volume of sterile water, and the resulting suspension was dropped into liquid nitrogen to obtain frozen cells.

10 g of the frozen cells, which had been subjected to the PAL induction treatment for 2 hours, were added to liquid nitrogen in a mortar and finely ground with a pestle. Then, as soon as the liquid nitrogen evaporated spontaneously and the ground frozen material began to thaw, 50 ml of buffer solution C [composed of 0.1M $Na_2HPO_4$ (pH 7.4), 0.15M sodium chloride, 1% sodium deoxycholate and 1% Triton X-100] containing 5% SDS was added thereto and gently stirred for 30 minutes.

After completion of the stirring, 50 ml of a phenol-chloroform mixture (composed of phenol, chloroform and isoamyl alcohol in a volume ratio of 25:24:1) was added thereto and mixed therewith by stirring for 15 minutes.

The resulting mixture was centrifuged and the aqueous phase was recovered. To this aqueous phase was added 50 ml of fresh phenol-chloroform mixture, followed by stirring for 15 minutes. After centrifugation, the aqueous phase was recovered again. Subsequently, this procedure for extraction with the phenol-chloroform mixture was repeated twice more.

To the finally obtained aqueous phase was added 5M sterile saline so as to give a final sodium chloride concentration of 0.2M. Then, 2.5 volumes of cold ethanol was added thereto. The resulting mixture was stored at −20° C. or below to precipitate the nucleic acid components.

The precipitate so formed was collected by centrifugation, washed with cold ethanol, and then dried under reduced pressure.

The dry material thus obtained was dissolved in 10 ml of sterile water, and the resulting solution was heat-treated at 65° C. for 5 minutes. Thereafter, mRNA was isolated according to Maniatis' method using oligo-d(T) cellulose [Maniatis, T., et al., "Molecular Cloning" (1982)].

The mRNA thus obtained was dissolved in a sample buffer solution (composed of 5M urea, 1 mM EDTA and 0.05% Bromophenol Blue) and then heat-treated at 65° C. for 2 minutes to destroy its higher-order structure. Thereafter, using an 8M urea-acrylamide slab gel (having an acrylamide concentration of 3% and containing 8M urea), the mRNA was electrophoresed at 100 volts for 1.5 hours in an electrophoretic buffer solution (composed of 89 mM Tris, 89 mM boric acid and 2 mM EDTA).

After completion of the electrophoresis, the acrylamide gel was treated with ethidium bromide and mRNA bands were visualized under ultraviolet light. The gel portion corresponding to an mRNA size range of 2.0 to 3.0 kb was divided into three equal parts in the lengthwise direction, and three gel segments were cut out of the slab gel.

Each gel segment was sealed in a dialysis tube, which was immersed in an electrophoretic buffer solution having the aforesaid composition. Thus, the mRNA was electrically eluted from the gel segment.

To the liquid inside each dialysis tube was added a phenolchloroform mixture. The resulting mixture was extracted twice with water and the aqueous phase thus obtained was further extracted with ether to remove any residual phenol. To this aqueous phase were added 1/10 volume of a 3M aqueous solution of sodium acetate (pH 5.2) and then 2.5 volumes of cold ethanol. The resulting mixture was stored at −20° C. to precipitate the mRNA.

In order to determine whether the mRNA fraction purified from each gel segment contained the mRNA for PAL or not, the mRNA contained in each fraction was translated into proteins and the produced proteins were tested with an antibody specific for PAL.

More specifically, each mRNA fraction was subjected to experiments with a cell-free translation kit using the lysate of rabbit reticulocytes [Pelham, H.R., et al., *European J. Biochem.*, 67, 247–256 (1976)].

The rabbit reticulocyte assay kit used was a product of Promega Biotec Co. and the labeled amino acid used was $^{35}$S-methionine (a product of Amersham Co.).

The PAL included in the proteins synthesized in the in vitro rabbit reticulocyte translation system was identified as follows: to the translation mixture was added buffer solution C in order to dissolve the proteins. After the insoluble matter was removed by centrifugation, self-prepared anti-PAL rabbit IgG was added to the supernatant and this reaction mixture was allowed to stand on ice for 30 minutes. Then, anti-rabbit IgG goat serum (self-prepared) was added to the reaction mixture, followed by standing on ice for 30 minutes. Thus, proteins were precipitated together with the rabbit antibody.

The precipitate was recovered by centrifugation, washed twice with buffer solution C, and then dissolved in a solution formed by mixing a mixture of 2% SDS and 10% 8-mercaptoethanol solution with a mixture of 0.1M Tris-phosphate (pH 6.8), 1% SDS and 50% glycerol solution in a volume ratio of 3:1. This reaction mixture was heated at 95° C for 2 hours to sever the disulfide linkages of the proteins. Then, the reaction mixture was subjected to SDS-polyacrylamide slab gel electrophoresis (at an acrylamide concentration of 10%) according to Laemmli's method [Laemmli, U.K., *Nature*, 227, 680–685 (1970)]. After completion of the electrophoresis, the gel was dried and PAL was detected by autoradiography.

Each of the aforesaid mRNA fractions was tested according to the above-described procedure. Thus, the fraction containing the mRNA for PAL was determined.

2. Conversion of the mRNA for PAL to double-stranded cDNA (ds-cDNA)

The fraction from the gel segment containing the mRNA for PAL, which had been obtained from the cells subjected to 2 hours' treatment for the induction of PAL as described in Section 1 above, was purified. The mRNA thus obtained was treated with AMV reverse transcriptase to convert it to a single-stranded cDNA molecule [Gugger, U., et al., *Gene*, 25, 263–269 (1983)].

More specifically, a single-stranded cDNA-mRNA hybrid was formed and then treated with RNaseH, DNA polymerase I and a ligase. Thus, the mRNA was removed and, at the same time, double-stranded cDNA (ds-cDNA) was constructed.

3. Construction of ds-cDNA having an Oligo-dC Tail Added to its 3'-Terminus

The ds-cDNA obtained in Section 2 above was treated with terminal deoxynucleotidyl transferase (TdT) to add an oligo-dC tail to the 3'-termini of the ds-cDNA.

More specifically, 3 μg of the ds-cDNA was dissolved in a reaction medium containing a TdT buffer solution [composed of 100mM potassium cacodylate (pH 7.2), 2 mM cobalt chloride and 0.2 mM dithiothreitol] and 0.2 mM dCTP, and pretreated at 37° C. for 5 minutes. Then, 50 units of TdT was added and the resulting reaction mixture was incubated at 37° C. for 15 minutes so as to allow the reaction to proceed. Thereafter, EDTA was added to a final concentration of 40 mM and the reaction mixture was placed on ice. Then, the TdT was denatured and inactivated by the addition of a phenol-chloroform mixture. After the denatured insoluble protein was removed from the reaction mixture by centrifugation, the supernatant was extracted with phenol and the separated aqueous phase was mixed with cold ethanol. The precipitate so formed was collected, washed with 70% ethanol, and then dried under reduced pressure to obtain ds-cDNA having an oligo-dC tails added to its 3'-terminus.

4. Construction of a Hybrid Plasmid

[Joining of a pUC9 molecule (having an oligo-dG tail) to a ds-cDNA molecule (having an oligo-dC tail)]

The oligo-dC tailed ds-cDNA obtained in Section 3 above was joined to the plasmid pUC9 (having an oligo-dG tail; readily available from Pharmacia Co., Sweden) according to Maniatis' method that is known as the dC-dG homopolymer method.

5. Transformation and Selection of Clones

The hybrid plasmid obtained in Section 4 above (consisting of an oligo-dG tailed pUC9 molecule and an oligo-dC tailed ds-cDNA molecule) was introduced into CaCl$_2$-treated *E. coli* [MC 1061; Casadaban, M.T., et al., *Method in Enz.*, Vol. 100, 293–308, Academic Press, New York (1983)] according to the competent cell method.

From about 40,000 transformant colonies obtained in the above-described manner, transformed cells were selected according to a colony hybridization method based on the procedure of Grunstein et al. [Grunstein, M., et al., *Proc. Natl. Acad. Sci. U.S.A.*, 72, 3961 (1971)].

As the probe for this colony hybridization, there was used the $^{32}$P-labeled single-stranded cDNA which had been obtained by forming single-stranded cDNA in the same manner as described in Section 2 above, except that, in place of dCTP, $\alpha$-$^{32}$P-dCTP was added to the reaction mixture.

From the positive colonies thus obtained, plasmids were extracted and purified. These plasmids were cleaved with various restriction endonucleases, and the sizes of the resulting DNA fragments were analyzed by agarose gel electrophoresis.

6. Construction of ds-cDNA Containing the Complete Structural Gene for PAL

Plasmids pSW2 and pSW11 were isolated from the transformants obtained in Section 5 above.

Moreover, as a result of the analysis carried out in Section 5 above by using various restriction endonucleases, it was found that the complete cDNA having the full length corresponding to the mRNA for PAL could be constructed by combining pSW2 with pSW11. Thus, each of these plasmids was extracted and purified from transformed cells containing it. The plasmids obtained from cells containing pSW2 were cleaved with the restriction endonuclease BanIII, and then with the restriction endonuclease HindIII. The resulting fragment mixture was fractionated by agarose gel electrophoresis. Thus, a DNA fragment having a size of 4.2 kb was recovered and purified by subjecting it several times to a procedure comprising treatment with a phenol-chloroform mixture and precipitation with cold ethanol.

On the other hand, the plasmids obtained from cells containing pSW11 were cleaved with the restriction endonucleases BanIII and HindIII. By subjecting the resulting fragment mixture to electrophoresis, a DNA fragment having a size of 0.8 kb was recovered and purified.

These 4.2 kb and 0.8 kb DNA fragments were cyclized with a ligase, and the resulting product was used to transform *E. coli* [JM83 (ATCC 35607); Messing, J., and Vieira, J., *Gene*, 19, 259–268 (1982)].

Plasmids were extracted from the transformants exhibiting ampicillin resistance used as the marker, and then treated with various restriction endonucleases to construct cleavage maps. Thus, a plasmid pSW13 having the full length PAL structure shown in the restriction endonuclease cleavage maps of FIGS. 1 and 3 was selected.

7. Determination of Nucleotide Sequence of Cloned DNA

The aforesaid plasmid pSW13 was isolated from a clone containing it, and this cloned DNA fragment was cleaved with various restriction endonucleases. With suitable restriction fragments, their nucleotide sequences were analyzed by Maxam-Gilbert's method (chemical decomposition method), and also biochemically by Maat's dideoxy method [Maat, J., et al., *Nucleic Acids Research*, 5, 4537–4545 (1978)]. The resulting nucleotide sequences of the respective DNA fragments were edited by use of the GENAS program produced by Mitsui Information Development Co. The nucleotide sequence so determined is shown in FIGS. 2(A)–(D).

The structural gene for PAL including its initiator codon and terminator codon comprises the base sequence extending from 1 to 2151 in FIGS. 2(A)–(D).

8. Construction of pSW101 (See FIG. 3)

In 14 $\mu$l of a reaction medium [composed of 7 mM Tris-HCl (pH 7.5), 0.7 mM EDTA, 7 mM MgCl$_2$, 175 mM NaCl, 7 mM $\beta$-mercaptoethanol and 0.01% bovine serum albumin (hereinafter abbreviated as BSA)], 0.9 $\mu$g of the plasmid pUC13 (a product of Pharmacia Co.) was treated with 10 units of the restriction endonuclease SalI at 37° C. for 16 hours. Subsequent treatment with a phenol-chloroform mixture and precipitation with ethanol gave linear DNA.

Then, in a nick translation buffer solution [composed of 50 mM Tris-HCl (pH 7.5), 10mM MgCl$_2$, 0.1 mM dithiothreitol, 2% BSA, 80$\mu$M dATP, 80$\mu$M dGTP, 80$\mu$M dTTP and 80$\mu$M dCTP], this linear DNA was treated with the Klenow fragment of DNA polymerase (a product of Takara Shuzo K.K.) at room temperature for 30 minutes. Thus, its cohesive ends were converted to flush ends. After deproteinization with phenol, DNA was precipitated with cold ethanol and recovered. By treating this DNA fragment with a phosphodiesterase derived from calf spleen (CIP; a product of Bohringer ö Co.), the 5'-terminal phosphoryl groups were removed to prevent self-cyclization of the linear pUC13.

On the other hand, the plasmid pSW13 was extracted and purified from cells containing it. In a reaction medium [composed of 4mM Tris-HCl (pH 7.5), 0.4 mM EDTA and 50 mM NaCl), the plasmid pSW13 was treated with the restriction endonuclease DraI at 37° C. for 28 hours. Then, after saline was added thereto so as to give a sodium chloride concentration of 100 mM, the plasmid pSW13 was further treated with the restriction endonucleases EcoRI and HindIII at 37° C. for 16 hours.

After completion of the treatment, the reaction mixture was subjected to agarose gel electrophoresis, and a DNA fragment having a size of 2.3 kb was recovered from the gel. Then, this DNA fragment was subjected three times to a procedure comprising extraction with phenol, treatment with a phenolchloroform mixture, and precipitation with cold ethanol. Thus, there was obtained a cDNA fragment coding for PAL.

In the aforesaid nick translation buffer solution, the cDNA fragment was treated with the Klenow fragment of DNA polymerase at room temperature for 45 minutes, and then subjected three times to a procedure comprising treatment with a phenol-chloroform mixture and precipitation with cold ethanol. Thus, there was obtained a cDNA fragment having flush ends.

Then, a circular plasmid pSW101 was constructed by joining the flush-ended pUC13 fragment to the flushended cDNA fragment by means of a ligase.

Using this hybrid DNA plasmid, *E. coli* (JM83) was transformed according to the well-known method. A cell strain (MT-10410, FERM BP-1710) was selected from among ampicillin-resistant colonies, and its PAL activity was determined.

Construction of pYtrp6 and Transformation

The plasmid pSW101 constructed in the manner described in Section 8 above was digested with PstI and BamHI. After the resulting fragment mixture was subjected to agarose gel electrophoresis, a DNA fragment of 370bp was recovered. This fragment was divided into two parts, and one of them was digested with BanI and the other with BbeI.

After digestion, the resulting fragment mixtures were subjected to acrylamide gel electrophoresis. Thus, a fragment having a size of 70 bp was recovered from the BanI digest and a fragment having a size of 280 bp was recovered from the BbeI digest.

The 70 bp fragment was treated with DNA polymerase to generate flush ends, to which ClaI(BanIII) linkers were joined by means of a ligase.

Figure 5:
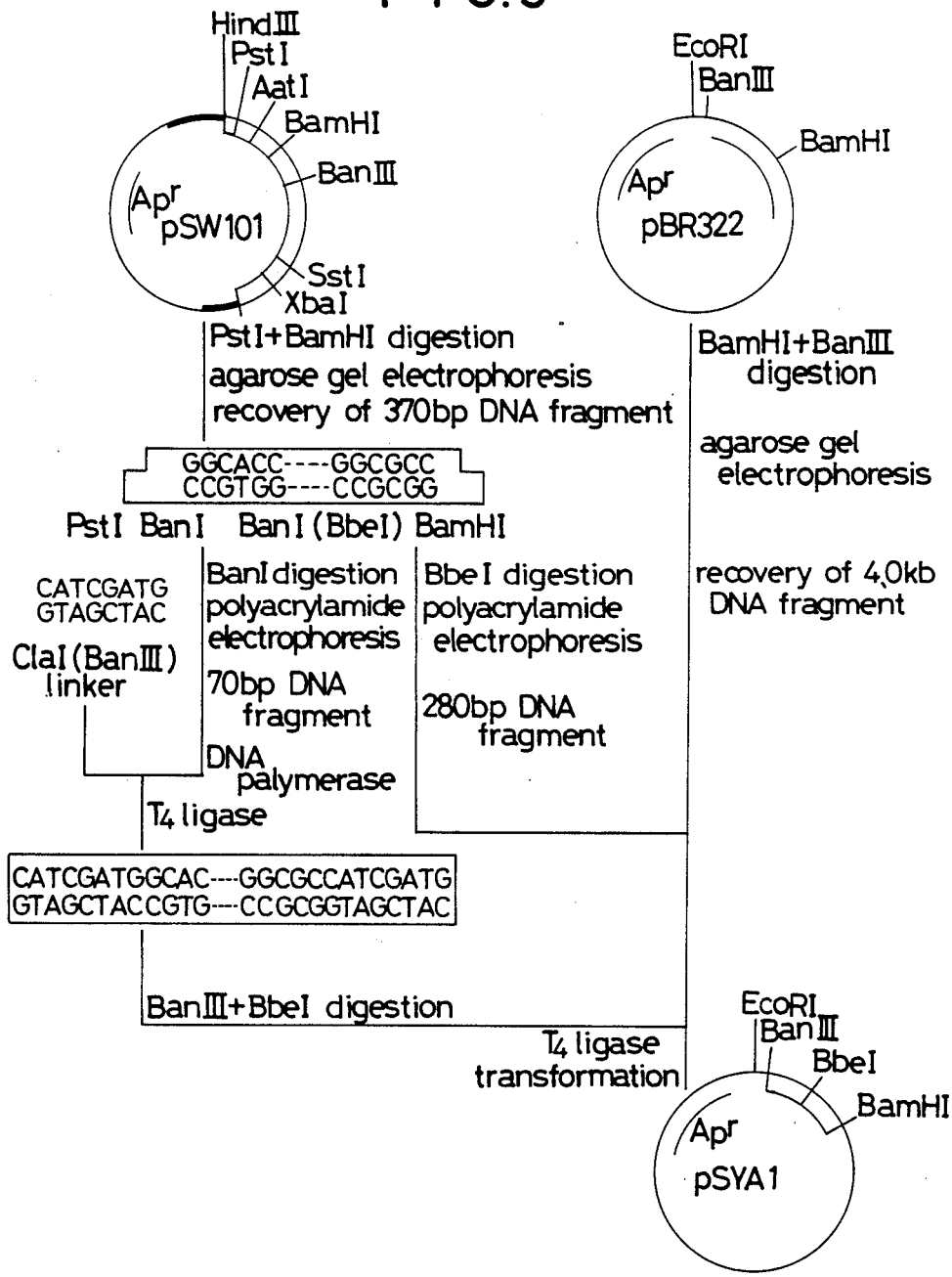
FIGS. 5 to 7 are flow charts illustrating the respective parts of the flow chart of FIG. 4 in more detail.

This DNA fragment having ClaI linkers joined to its both ends was digested with BanIII and BbeI. On the other hand, pBR322 was digested with BanIII and BamHI, and a DNA fragment of 4.0 kb was recovered by agarose gel electrophoresis. Then, as illustrated in FIG. 5, the aforesaid BanIII+BbeI fragment and the previously prepared BbeI fragment (280 bp) were joined to the pBR322 fragment (4.0 kb) by means of a ligase. Thus, there was obtained a plasmid pSYA1. Then, E. coli (MC1061) was transformed with pSYA1 according to the well-known calcium method. E. coli carrying pSYA1 was inoculated into 3 ml of LB medium containing ampicillin and incubated at 37° C. overnight. The grown cells were collected by centrifugation and suspended in 60 μl of a solution composed of 50 mM glucose, 25 mM Tris-HCl (pH 8.0) and 10 mM EDTA to form a cell suspension. Then, 40 μl of a 10 mg/ml lysozyme solution was added thereto and the resulting reaction mixture was allowed to stand at room temperature for 5 minutes. After completion of the reaction, 200 μl of 0.2 N NaOH containing 1% SDS was added thereto. After gentle vortexing, the reaction mixture was placed on ice and allowed to stand for 5 minutes. Then, 150 μl of a 5 M sodium acetate solution (pH 4.8) was added thereto. After gentle vortexing, the reaction mixture was placed on ice to stop the reaction.

The resulting lysate was centrifuged at 12,000 rpm for 10 minutes and the supernatant was separated. Then, this supernatant was subjected three times to a procedure comprising treatment with a phenol-chloroform mixture and precipitation with cold ethanol.

From the precipitate thus obtained, pSYA1 was extracted according to conventional procedure. After pSYA1 was digested with BamHI and BanIII, a DNA fragment having a size of 350 bp was recovered.

Separately, the plasmid pSW13 constructed in Section 6 above was digested with XbaI and the resulting cohesive ends were treated with DNA polymerase to generate flush ends. Then, a HindIII linker was joined thereto by means of a ligase to construct pSW13H. Then, this pSW13H was digested with BamHI and HindIII. By subjecting the resulting DNA fragment mixture to agarose gel electrophoresis, a DNA fragment having a size of 1.9 kb was recovered.

On the other hand, the plasmid pVV1 [Brian P. Nicols and Charles Yanofsky, Methods in Enzymology, 101, 155 (1983)] containing a part of the trp operon of E. coli was digested with the restriction endonuclease HinfI.

The DNA fragments of the digested plasmid were separated by agarose gel electrophoresis, and a DNA fragment having a size of 0.9 kb was recovered from the gel according to the previously described procedure.

The cohesive ends of the 0.9 kb DNA fragment generated by digestion with HinfI were converted to flush ends according to the procedure described in Section 8 above. Then, an EcoRI linker (GGAATTCC) was joined to the 5'-flush end by means of a ligase.

The DNA fragment having an EcoRI linker jointed thereto was treated with the restriction endonuclease EcoRI to create a DNA fragment having an EcoRI-cleaved cohesive end [Brian P. Nicols and Charles Yanofsky, Methods in Enzymology, 101, 155 (1983)].

Using a ligase, the DNA fragment having an EcoRI cohesive end was joined to a DNA fragment which had been obtained by treating the EcoRI digest of pBR322 with CIP according to the procedure described in Section 8 above. The resulting product was digested with the restriction endonucleases EcoRI and BglII. By subjecting the resulting digest to agarose gel electrophoresis, a DNA fragment having a size of 0.4 kb was separated and recovered.

This DNA fragment, which had three cleavage sites for the restriction endonuclease TaqI, was partially digested with TacI. Thus, a DNA fragment having a size of 345 bp was recovered.

This 345 bp DNA fragment was joined to a 4.3 kb DNA fragment obtained by digesting pBR322 with EcoRI and ClaI. Thus, there was obtained a plasmid pFtrp2 containing the trp promoter.

Figure 6:
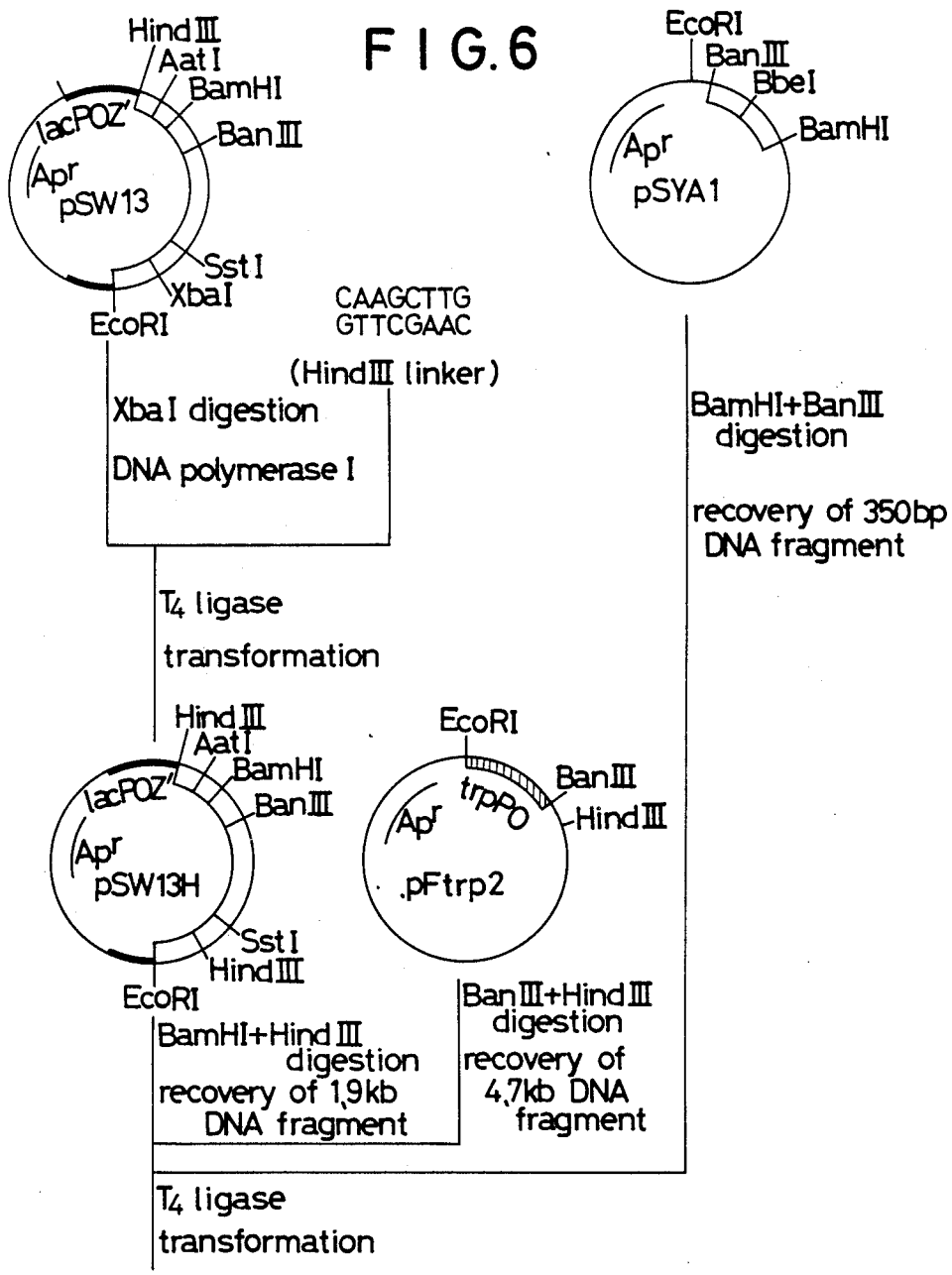
Figure 7:
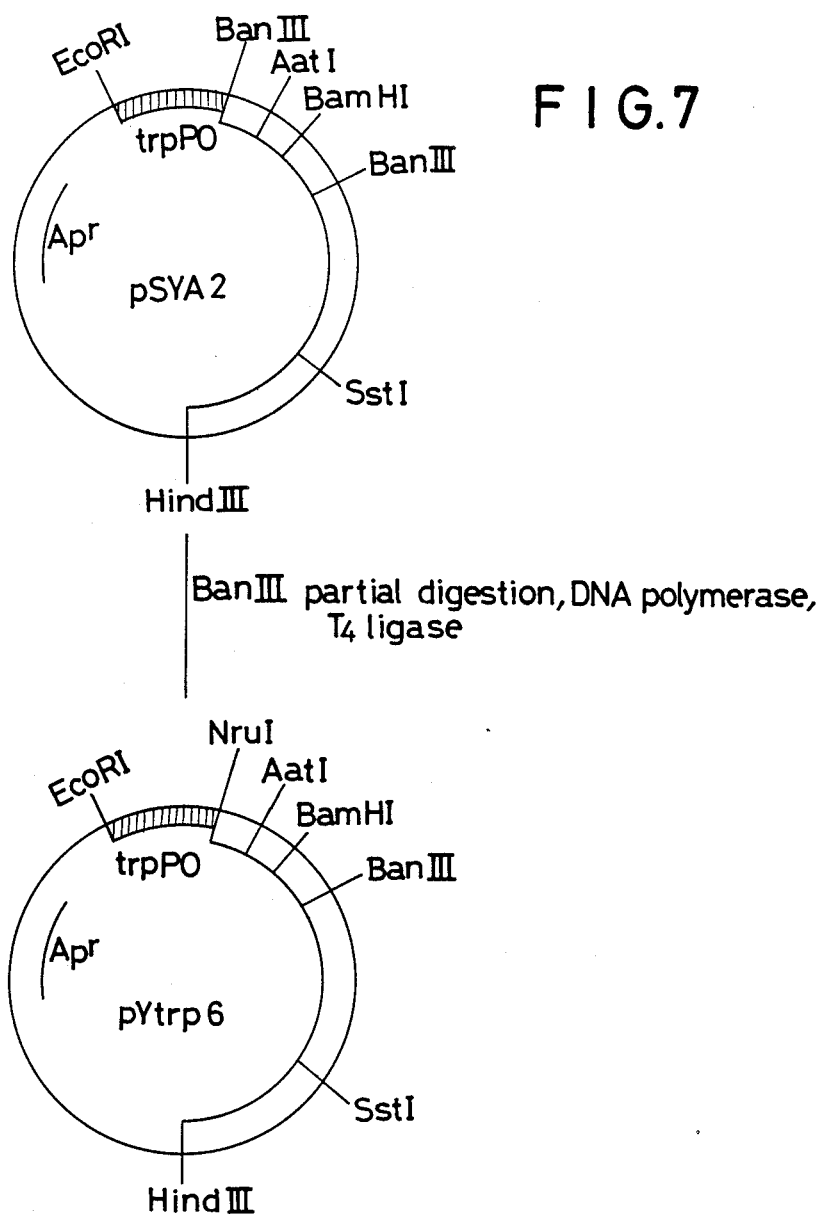

The plasmid pFtrp2 constructed in the abovedescribed manner was digested with BanIII and HindIII. By subjecting the resulting fragment mixture to agarose gel electrophoresis, a fragment of 4.7 kb was recovered. Then, as illustrated in FIG. 6, this 4.7 kb fragment were joined to the previously prepared BamIII+BamIII fragment of 350 bp and the previously prepared BamHI+HindIII fragment of 1.9 kb by means of a ligase. Thus, a circular plasmid pSYA2 was constructed as illustrated in FIG. 7.

Furthermore, pSYA2 was partially digested with BanIII and the resulting cohesive ends were treated with DNA polymerase to generate flush ends. Then, this fragment was cyclized by means of a ligase to create a plasmid pYtrp6 (FIG. 7) having a cleavage site for NruI.

Figure 4:
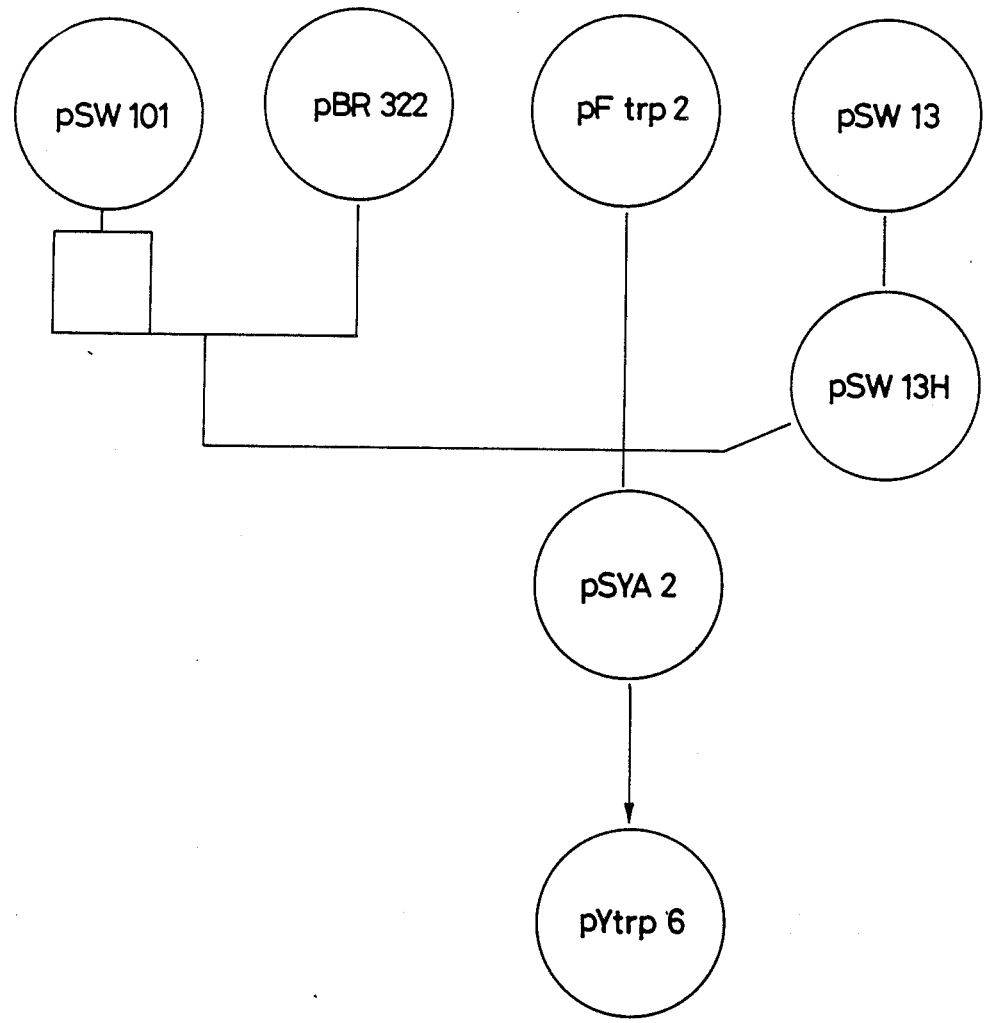
FIG. 4 is a flow chart illustrating the procedure for constructing the plasmid pYtrp6.

E. coli MC1061 was transformed with pYtrp6 according to the well-known method. Cells were selected from the resulting ampicillin-resistant colonies and then tested for PAL activity. The construction of pYtrp6 is generally illustrated in the flow chart of FIG. 4 and its greater details are illustrated in FIGS. 5 to 7. Thus, a transformed strain of E. coli exhibiting PAL activity was isolated and named MT-10414 (FERM BP-1712).

(EXAMPLES)

In order to afford a better understanding of the present invention, the following Example and Comparative Examples are given.

Figure 8:
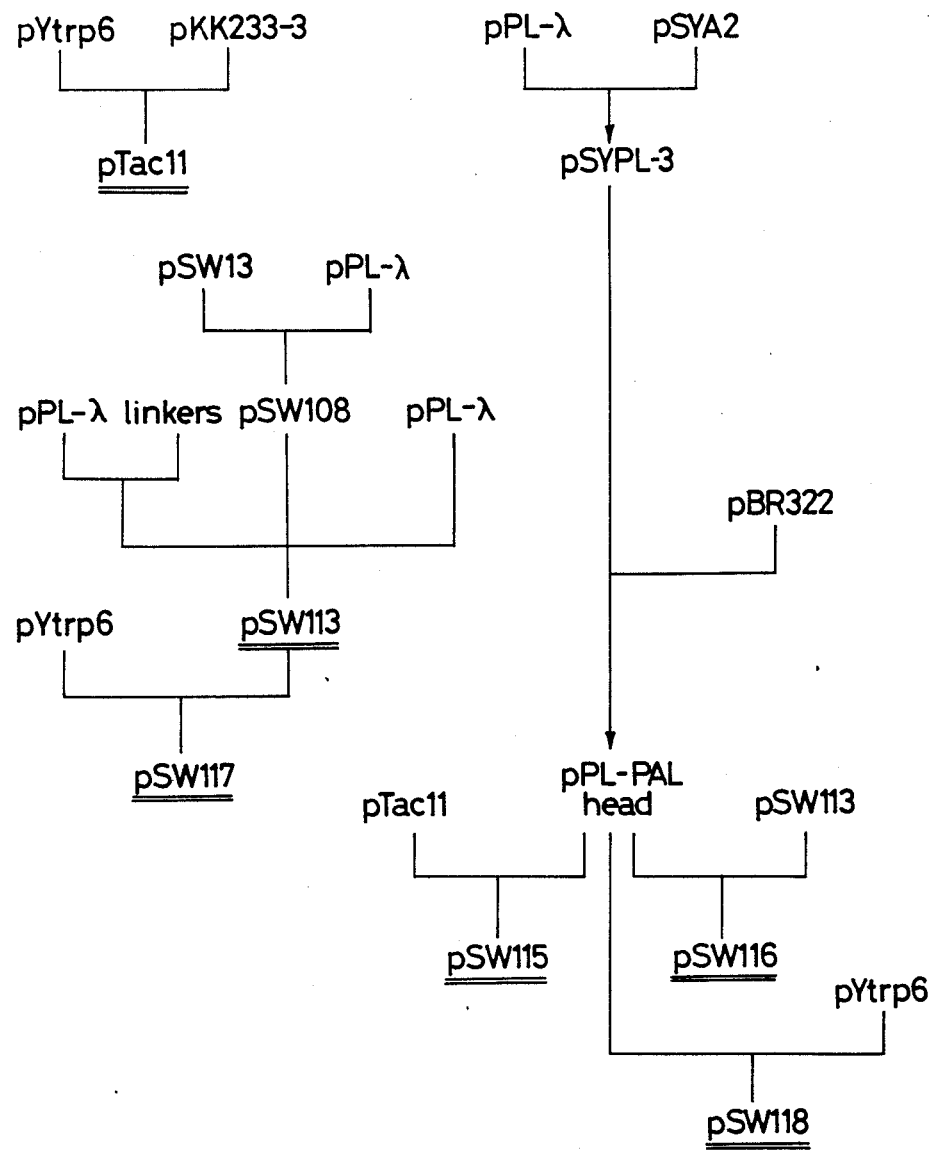
FIG. 8 generally illustrates the procedures for constructing various hybrid plasmids as described in Example 1 and Comparative Examples 1 to 3.

The procedures for constructing various plasmids in these Example and Comparative Examples are generally illustrated in FIG. 8.

EXAMPLE 1

[Construction of plasmid pSW115]

Figure 9:
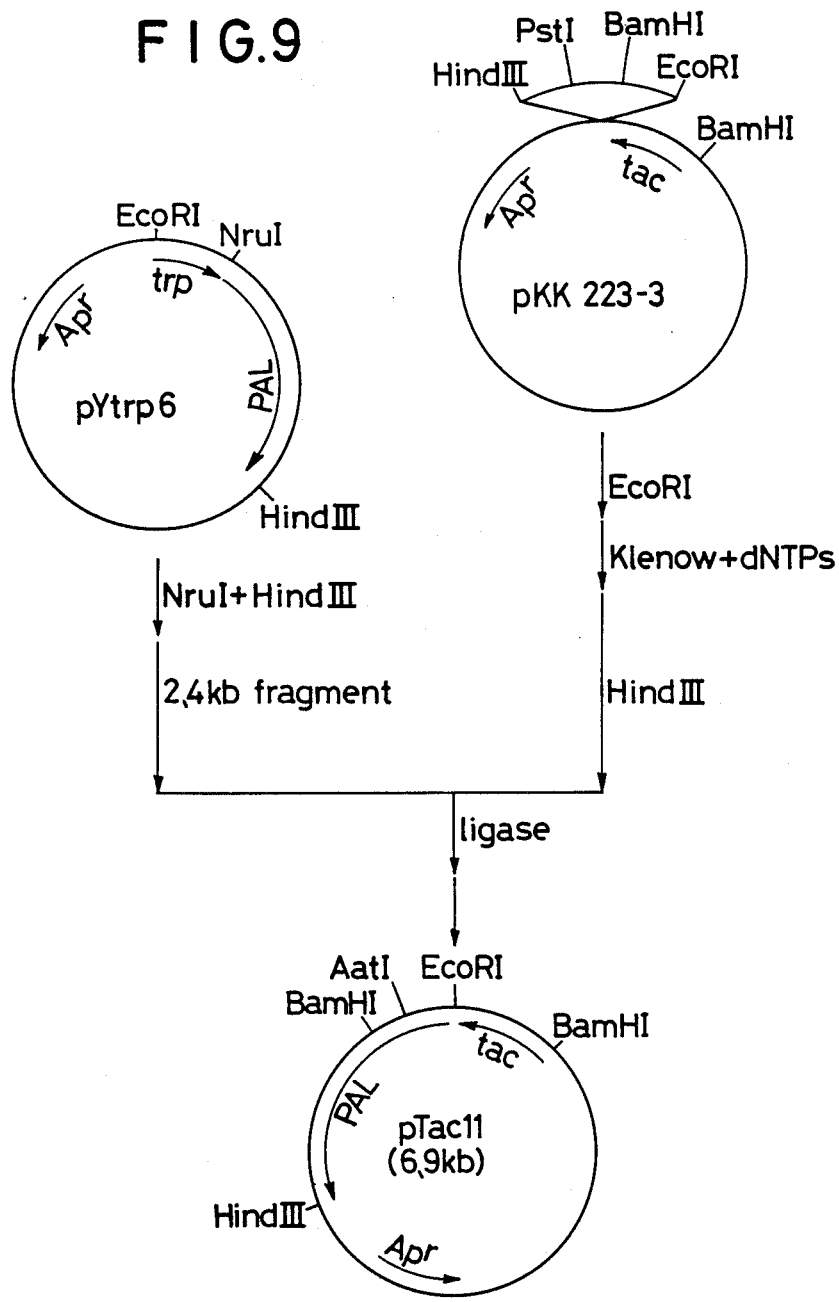
FIGS. 9 to 13 more specifically illustrates the procedures for constructing the plasmid pTacII, the plasmid pP$_L$-PAL-head, the plasmid pSW113, the plasmids pSW115 and pSW116, and the plasmids pSW117 and pSW118, respectively.

(1) Construction of plasmid pTacII according to the procedure illustrated in FIG. 9

First of all, plasmids were extracted from *E. coli* MT 10414 (FERM BP-1712) carrying the plasmid pYtrp6 in which the structural gene for PAL derived from *Rhodosporidium toruloides* was cloned according to the procedures described in Reference Example. These plasmids were digested with the restriction endonucleases NruI and HindIII. From the resulting DNA fragment mixture, a DNA fragment having a size of 2.4 kb was separated and recovered by electrophoresis.

Separately, the plasmid pKK223-3 (a product of Pharmacia Co.) having the tac promoter was digested with the restriction endonuclease EcoRI to obtain a DNA fragment. Then, using DNA polymerase, the cohesive ends of this DNA fragment was converted to flush ends.

Thereafter, the flush-ended DNA fragment was digested with HindIII to obtain a DNA fragment having cohesive ends. This DNA fragment was reacted with the previously prepared 2.4 kb DNA fragment in the presence of a ligase. The resulting reaction product was introduced into *E. coli* MC 1061 according to the method of S. N. Cohen et al.

Subsequently, *E. coli* having the reaction product introduced thereinto was grown on an ampicillin plate prepared by adding 1.5% of agar to LB medium [composed of 10 g of Bacto-tryptone ® (a product of Difco), 5 g of Bacto-yeast Extract ® (a product of Difco), 1 g of glucose and 1 liter of distilled water and adjusted to pH 7.5 with NaOH] containing ampicillin at a concentration of 50 μg/ml. After completion of the incubation, plasmids were extracted from each of the ampicillin-resistant colonies having appeared on the plate, and the restriction endonuclease cleavage map of each plasmid was constructed. Thus, the colonies containing the desired plasmid pTacII having the structure illustrated in FIG. 9 were identified, and the plasmid pTacII was isolated from these colonies.

Figure 10:
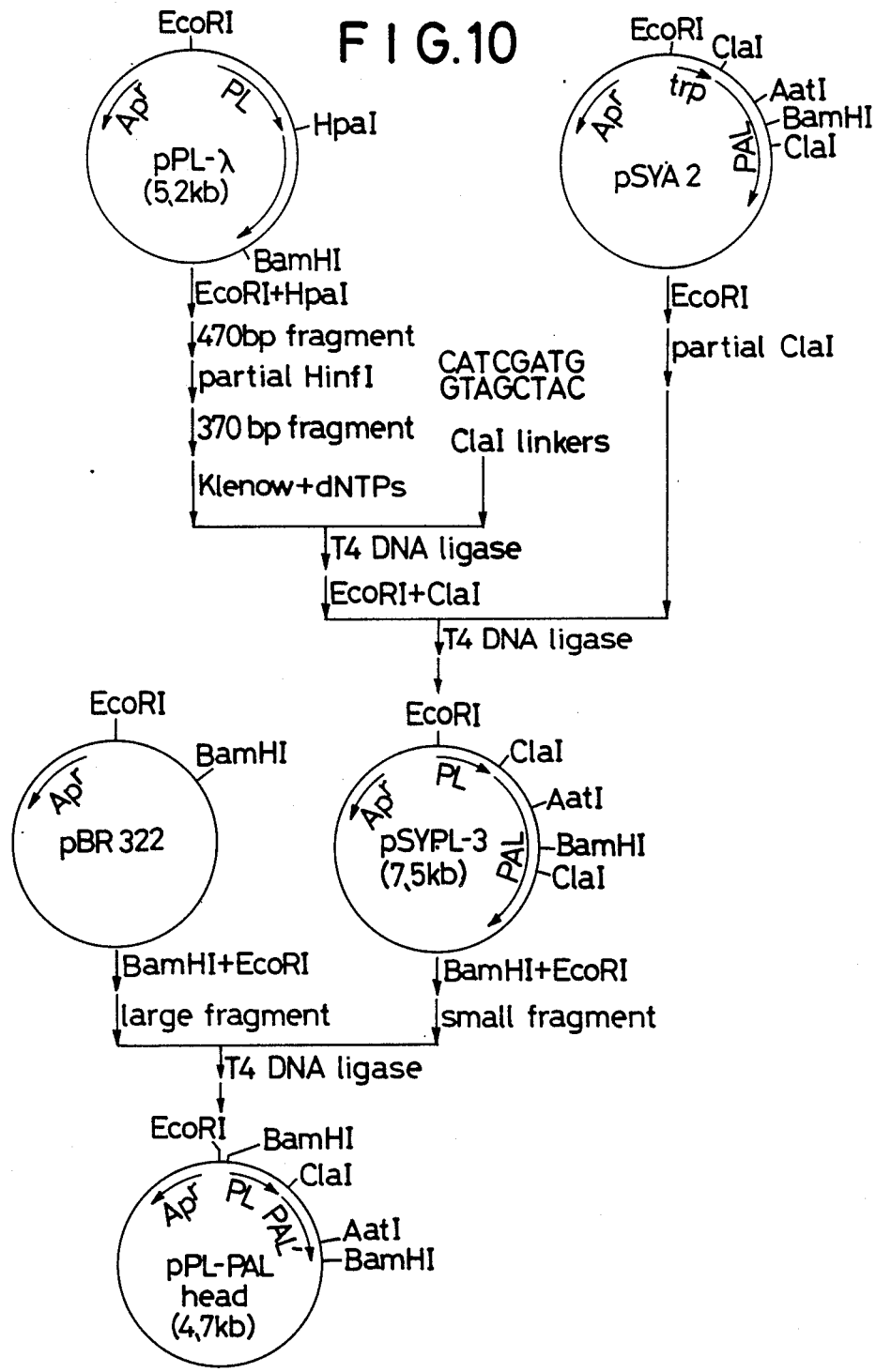

(2) Construction of plasmid pP$_L$-PAL-head according to the procedure illustrated in FIG. 10

The plasmid pP$_L$-λ (a product of Pharmacia Co.) was digested with the restriction endonucleases EcoRI and HpaI. From the resulting DNA fragment mixture, a DNA fragment of 470 bp was separated and recovered by electrophoresis. Then, this 470 bp DNA fragment was partially digested with the restriction endonuclease HinfI. From the resulting DNA fragment mixture, a DNA fragment of 370 bp was separated and recovered by electrophoresis.

Furthermore, the termini of this 370 bp DNA fragment were treated with DNA polymerase to generate flush ends, which were reacted with ClaI linkers (a product of Takara Shuzo K.K.) in the presence of a ligase. After completion of the reaction, the resulting reaction product was digested with the restriction endonucleases EcoRI and ClaI to obtain a mixture containing an EcoRI-ClaI DNA fragment.

Separately, the plasmid pSYA2, which had been constructed in the process of cloning of the structural gene for PAL of *Rhodosporidium toruloides* in the previously given Reference Example, was digested with the restriction endonuclease EcoRI. Furthermore, the resulting DNA fragment was partially digested with the restriction endonuclease ClaI. From the resulting mixture of two (large and small) DNA fragments, the large DNA fragment was extracted and separated by electrophoresis.

Then, this large DNA fragment derived from the plasmid pSYA2 was reacted with the previously prepared mixture containing an EcoRI-ClaI fragment, in the presence of T$_4$ ligase. The resulting reaction products were introduced into *E. coli* MC1061, which was grown on an ampicillin plate. Then, plasmids were prepared from each of the colonies having appeared on the plate, and their restriction endonuclease cleavage maps were constructed. Thus, the colonies containing the desired plasmid pSYP$_L$-3 having the structure illustrated in FIG. 10 were identified, and the plasmid pSYP$_L$-3 was isolated from these colonies. Thus, a transformed *E. coli* strain carrying plasmid pSYP$_L$-3 capable of producing PAL was isolated and named MT-10424 (FERM BP-1714).

Furthermore, the plasmid pSYP$_L$-3 thus obtained was digested with EcoRI and BamHI. From the resulting mixture of two (large and small) DNA fragments, the small DNA fragment was separated and recovered by electrophoresis.

Separately, the plasmid pBR322 (a product of Pharmacia Co.) was digested with the restriction endonucleases EcoRI and BamHI. From the resulting mixture of two (large and small) DNA fragments, the large DNA fragment was separated and recovered by electrophoresis. Then, this large DNA fragment was reacted with the small fragment previously prepared from the plasmid pSYP$_L$-3, in the presence of a ligase. Thus, there was obtained a plasmid pP$_L$-PAL-head having the structure illustrated in FIG. 10. In order to confirm that the desired plasmid was obtained, the reaction product resulting from the aforesaid reaction in the presence of a ligase was introduced into *E. coli* MC 1061, which was grown on an ampicillin plate. Then, plasmids were prepared from each of the colonies having appeared on the plate, and their restriction endonuclease cleavage maps were constructed.

Figure 12:
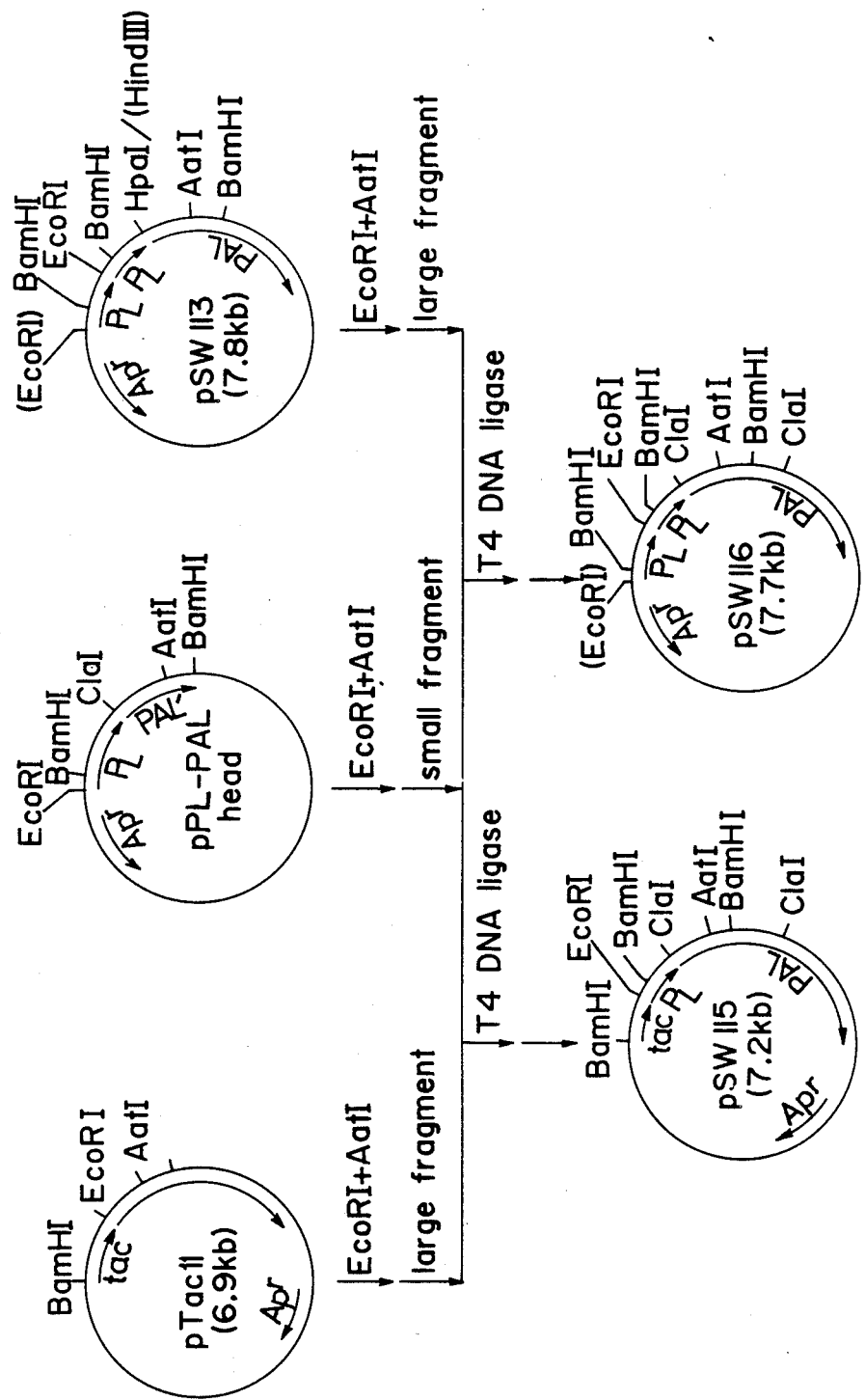

(3) Construction of plasmid pSW115 according to the procedure illustrated in FIG. 12

First of all, the plasmid pTacII obtained in Section (1) above was digested with the restriction endonucleases EcoRI and AatI. From the resulting mixture of two (large and small) DNA fragments, the large DNA fragment was separated and recovered by electrophoresis.

Then, the plasmid pP$_L$-PAL-head obtained in Section (2) above was digested with the restriction endonucleases EcoRI and AatI. From the resulting mixture of two (large and small) DNA fragments, the small DNA fragment was separated and recovered by electrophoresis.

Finally, the aforesaid large DNA fragment derived from the plasmid pTacII was joined to the aforesaid small DNA fragment derived from the plasmid pP$_L$-PAL-head, by reacting them in the presence of T$_4$ ligase. Thus, there was obtained a plasmid pSW115.

In order to confirm that the desired plasmid was obtained, the plasmid produced by the aforesaid reaction was introduced into *E. coli* MC 1061 and the resulting transformants were selected on an ampicillin plate. Then, plasmids were prepared from the respective transformants and their restriction endonuclease cleavage maps were constructed. At the same time, these transformants were tested for PAL activity according to the procedure described later. Thus, a transformed *E. coli* strain carrying plasmid pSW115 having PAL activity was obtained and named MT-10423 (FERM BP-1714).

(4) Expression of PAL by use of plasmid pSW115

The transformed strain of *E. coli* obtained in Section (3) above, into which the plasmid pSW115 had been introduced, was inoculated into a culture medium prepared by adding ampicillin to LB medium (pH 7.5), as previously used in the preparation of ampicillin plate, so as to give a concentration of 50 μg/ml. The inoculated medium was shaken at 30° C.

After 20 hours' incubation, the culture exhibited such a cell concentration as to give an optical density (O.D.) of 5.40 at 660 nm. Thus, cells were collected from the culture by centrifugation and then tested for PAL activity according to the procedure described below. The specific activity per unit weight of dry cells was calculated and the result is shown in Table 2.

Determination of PAL activity:

Cells were collected from the culture by centrifugation. The collected cells were washed by suspending them in 0.85% saline and centrifuging the resulting suspension. Then, the washed cells were suspended in a 25mM Tris-HCl buffer solution (pH 8.8) so as to give a cell concentration of 1% on a wet weight basis. This suspension was added to an enzymatic reaction medium comprising a 25mM Tris-HCl buffer solution (pH 8.8) containing 25mM L-phenylalanine and 0.005% cetyl pyridinium hydrochloride. The resulting reaction mixture was incubated at 30° C. for 20 minutes. After the reaction was stopped by the addition of 1N HCl, the cinnamic acid formed in the reaction mixture was analyzed by liquid chromatography. Thus, the PAL activity was determined in terms of units. One unit (U) corresponds to the amount of the enzyme which forms 1 micromole of cinnamic acid in a minute.

The dry cell weight used to obtain the data shown in Table 2 was determined by drying a sample of the washed cells and then weighing it.

Comparative Example 1

Figure 11:
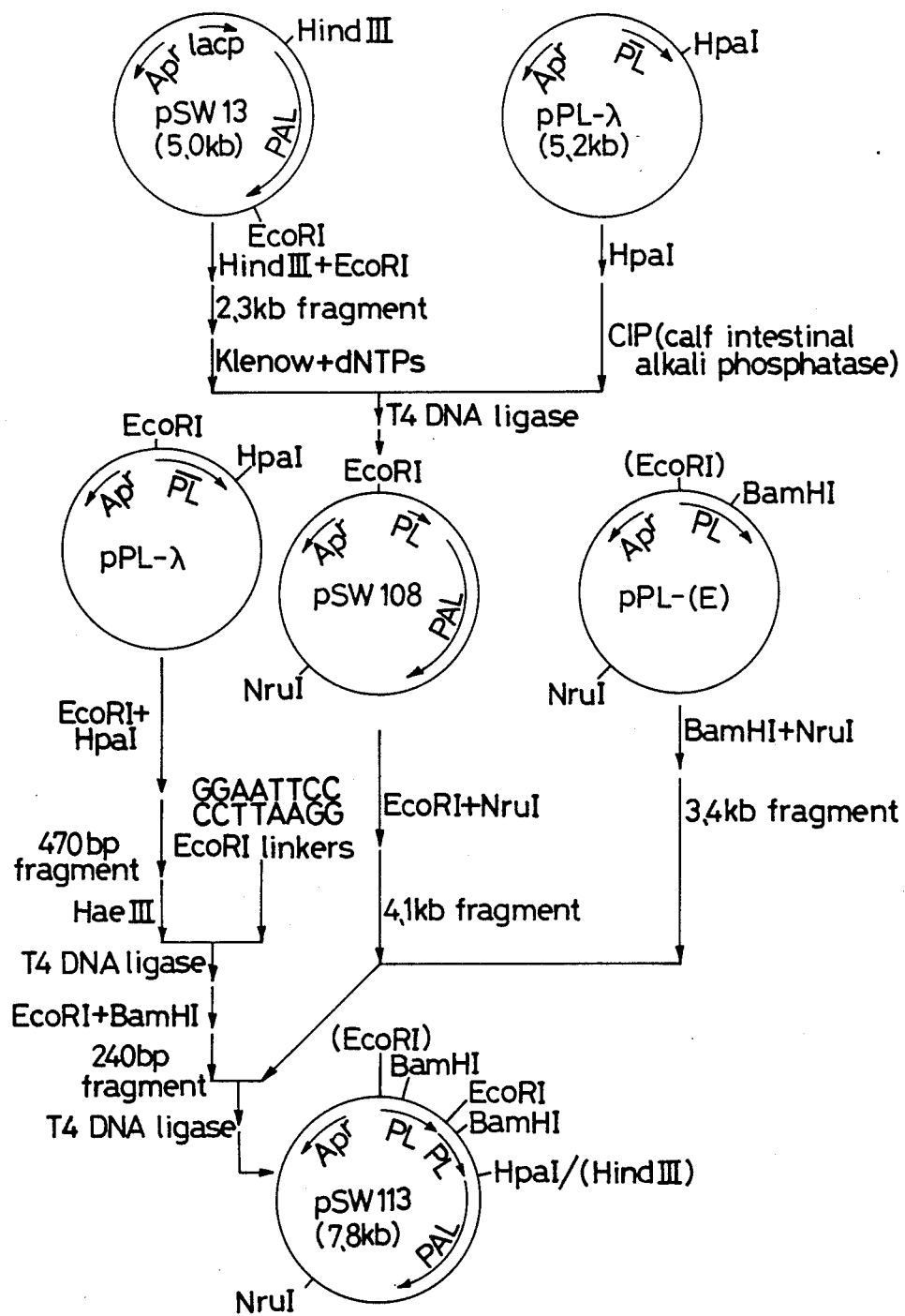

[Construction of plasmid pSW116 according to the procedure illustrated in FIGS. 11 and 12 and expression of PAL in *E. coli* by use of it]

(1) Construction of plasmid pSW108

First of all, the plasmid pSW13, which had been constructed in the process of cloning of the structural gene for PAL of *Rhodosporidium toruloides* as described in Reference Example, was digested with the restriction endonucleases HindIII and EcoRI. From the resulting DNA fragment mixture, a DNA fragment having a size of 2.3 kb was separated and recovered by electrophoresis. Then, the termini of this DNA fragment were treated with DNA polymerase to generate flush ends.

Separately, the plasmid pPL-λ (a product of Pharmacia Co.) was digested with the restriction endonuclease HpaI. The resulting DNA fragment was subjected to CIP treatment for the prevention of self-recombination according to the procedure of Maniatis et al. [T. Maniatis et al., "Molecular Cloning", a laboratory manual, 133, Cold Spring Harbor, New York (1982)]. Thereafter, this DNA fragment was reacted with the 2.3 kb DNA fragment previously prepared from the plasmid pSW13, in the presence of a ligase. After completion of the reaction, the resulting reaction product was introduced into *E. coli* MC 1061, which was grown on an ampicillin plate. Then, plasmids were prepared from each of the ampicillin-resistant colonies having appeared on the plate, and the restriction endonuclease cleavage map of each plasmid was constructed. Thus, the colonies containing the desired plasmid pSW108 having the structure illustrated in FIG. 11 were identified, and the plasmid pSW108 was isolated from these colonies.

(2) Construction of plasmid pP$_L$-[E]

The plasmid pP$_L$-λ (a product of Pharmacia Co.) was cleaved by digestion with the restriction endonuclease EcoRI. The termini of the resulting DNA fragment were treated with DNA polymerase to generate flush ends. Thereafter, this DNA fragment was cyclized with a ligase to obtain a plasmid pP$_L$-[E].

(3) Construction of plasmid pSW113

First of all, the plasmid pP$_L$-λ (a product of Pharmacia Co.) was digested with the restriction endonucleases EcoRI and HpaI. From the resulting DNA fragment mixture, a DNA fragment of 470 bp was separated and recovered by electrophoresis. Then, this 470 bp DNA fragment was digested with the restriction endonuclease HaeIII. The resulting reaction product was reacted with EcoRI linkers (a product of Takara Shuzo K.K.) in the presence of T$_4$ ligase. Then, the resulting reaction product was treated with the restriction endonucleases EcoRI and BamHI to obtain a mixture of DNA fragments. From this mixture of DNA fragments, a DNA fragment of 240 bp was separated and recovered by electrophoresis.

Separately, the plasmid pSW108 obtained in Section (1) above was digested with the restriction endonucleases EcoRI and NruI. From the resulting DNA fragment mixture, a DNA fragment of 4.1 kb was separated and recovered by electrophoresis.

Furthermore, the plasmid pPL-[E] obtained in Section (2) above was digested with the restriction endonucleases BamHI and NruI. From the resulting DNA fragment mixture, a DNA fragment of 3.4 kb was separated and recovered by electrophoresis.

Finally, the three DNA fragments obtained in the above-described manner were reacted in the presence of T$_4$ ligase The resulting reaction product was introduced into *E. coli* MC 1061, which was grown on an ampicillin plate. Then, plasmids were prepared from each of the ampicillin-resistant colonies having appeared on the plate, and their restriction endonuclease cleavage maps were constructed. At the same time, a portion of each colony was grown in the same manner as described in Example 1 and then tested for PAL activity. Thus, the colonies containing the desired plasmid pSW113 having the structure illustrated in FIG. 11 were identified, and the plasmid pSW113 was isolated from these colonies.

(4) Construction of plasmid pSW116

First of all, the plasmid pSW113 obtained in Section (3) above was digested with the restriction endonucleases EooRI and AatI. From the resulting mixture of two (large and small) DNA fragments, the large DNA fragment was separated and recovered by electrophoresis.

Separately, the plasmid pP$_L$-PAL-head obtained in Section (3) of Example 1 was digested with the restriction endonucleases EcoRI and AatI. From the resulting mixture of two (large and small) DNA fragments, the small DNA fragment was separated and recovered by electrophoresis.

Then, the two DNA fragments separated and recovered in the above-described manner were joined together by reacting them in the presence of T₄ ligase. Thus, there was obtained a plasmid pSW116 having the structure illustrated in FIG. 12.

In order to confirm that the desired plasmid was obtained, the restriction endonuclease cleavage map of the resulting plasmid was constructed and the resulting transformants were tested for PAL activity, in the same manner as described in Example 1.

(5) Expression of PAL by use of plasmid pSW116

The transformation of *E. coli* and the expression of PAL were carried out in the same manner as described in Section (4) of Example 1, except that the plasmid pSW116 obtained in Section (4) above was used. The specific activity of PAL so produced was calculated. The final cell concentration of the resulting culture of the transformed strain and the value of specific PAL activity are shown in Table 2.

COMPARATIVE EXAMPLE 2

[Construction of plasmid pSW117 and expression of PAL in *E. coli* by use of it]

Figure 13:
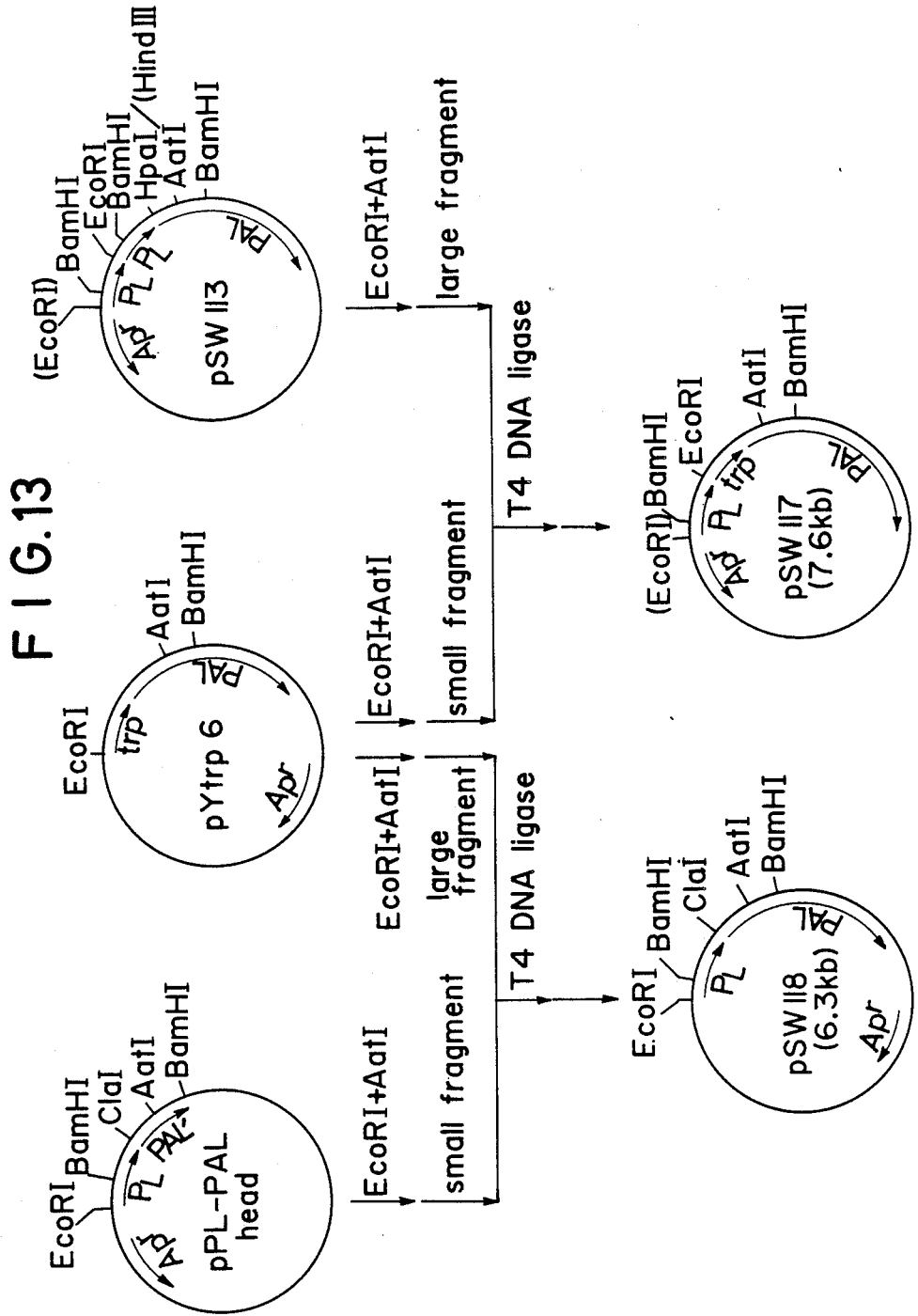

As illustrated in FIG. 13, the plasmid pSW113 obtained in Section (3) of Comparative Example 1 was digested with the restriction endonucleases EcoRI and AatI. From the resulting mixture of two (large and small) DNA fragments, the large DNA fragment was separated and recovered by electrophoresis.

Separately, the plasmid pYtrp6 used in Section (1) of Example 1 was digested with the restriction endonucleases EcoRI and AatI. From the resulting mixture of two (large and small) DNA fragments, the small DNA fragment was separated and recovered by electrophoresis.

Then, the two DNA fragments separated and recovered in the above-described manner were joined together by reacting them in the presence of T₄ ligase. Thus, there was obtained a plasmid pSW117 having the structure illustrated in FIG. 13.

In order to confirm that the desired plasmid was obtained, the restriction endonuclease cleavage map of the resulting plasmid was constructed and the resulting transformants were tested for PAL activity, in the same manner as described in Example 1.

Thereafter, the transformation of *E. coli* and the expression of PAL were carried out in the same manner as described in Section (4) of Example 1, except that the plasmid pSW117 obtained in the above-described manner was used. The specific activity of PAL so produced was calculated. The final cell concentration of the resulting culture of the transformed strain and the value of specific PAL activity are shown in Table 2.

COMPARATIVE EXAMPLE 3

[Construction of plasmid pSW118 and expression of PAL in *E. coli* by use of it]

As illustrated in FIG. 13, the plasmid pP$_L$-PAL-head obtained in Section (2) of Example 1 was digested with the restriction endonucleases EcoRI and AatI. From the resulting mixture of two (large and small) DNA fragments, the small DNA fragment was separated and recovered by electrophoresis.

Separately, the plasmid pYtrp6 used in Section (1) of Example 1 was digested with the restriction endonucleases EcoRI and AatI. From the resulting mixture of two (large and small) DNA fragments, the large DNA fragment was separated and recovered by electrophoresis.

Then, the two DNA fragments separated and recovered in the above-described manner were joined together by reacting them in the presence of T₄ ligase. Thus, there was obtained a plasmid pSW118 having the structure illustrated in FIG. 13.

In order to confirm that the desired plasmid was obtained, the restriction endonuclease cleavage map of the resulting plasmid was constructed and the resulting transformants were tested for PAL activity, in the same manner as described in Example 1.

Thereafter, the transformation of *E. coli* and the expression of PAL were carried out in the same manner as described in Section (4) of Example 1, except that the plasmid pSW118 obtained in the above-described manner was used. The specific activity of PAL so produced was calculated. The final cell concentration of the resulting culture of the transformed strain and the value of specific PAL activity are shown in Table 2.

In the above Example and Comparative Examples, the introduction of a recombinant plasmid in *E. coli* was carried out according to the method of S. N. Cohen et al. [S. N. Cohen et al., *Proc. Natl. Acad. Sci. USA*, 9, 2110 (1972)]. Unless otherwise specified, the treatment of plasmids or DNA fragments with a restriction endonuclease or endonucleases, ligase, T₄ ligase or DNA polymerase and the preparation of plasmids from bacterial cells were carried out in the publicly-known manner. Unless otherwise specified, the restriction endonucleases, ligase, T₄ ligase, linkers and DNA polymerase used were products of Takara Shuzo K.K.

TABLE 2

| Order of connection of promoters | Designation of plasmid | Turbidity of culture (O.D. at 660 nm) | PAL activity (U/g of dry cells) |
|---|---|---|---|
| tac-P$_L$ | pSW115 | 5.40 | 630 |
| P$_L$-P$_L$ | pSW116 | 4.40 | 390 |
| P$_L$-trp | pSW117 | 5.20 | 66 |
| P$_L$ | pSW118 | 4.75 | 345 |

Among the above-mentioned strains, those having an ATCC number have been deposited with the American Type Culture Collection, 12301 Parklawn Drive, Rockville, Md. 20852-1776, U.S.A.; that having an IFO number with the Fermentation Research Institute (Incorporated Foundation), 17-85, Juso-Motomachi 2-chome, Yodogawa-ku, Osaka City, Japan; and those having an FERM number with the Fermentation Research Institute of the Agency of Industrial Science and Technology, 1-3, Higashi 1-chome, Tsukuba-Shi, Ibaraki-Ken 305, Japan.

Those having an ATCC number and that having an IFO number are publicly available.

Those having an FERM number was deposited on the following date for patent purposes by the applicant.
  FERM BP-1710 on July 4, 1986;
  FERM BP-1712 on July 26, 1986;
  FERM BP-1713 on Oct. 31, 1986; and
  FERM BP-1714 on October 31, 1986.

What is claimed is:

1. A recombinant plasmid comprising:
(a) a vector capable of replicating in *Escherichia coli*;

(b) a combined promoter comprising the tac promoter and, the P_L promoter of the lambda phage, said P_L promoter being connected downstream of said tac promoter; and (c) a DNA sequence derived from *Rhodosporidium toruloides* coding for L-phenylalanine ammonia-lyase, said DNA sequence being operably linked to and inserted downstream of said combined promoter, whereby the two promoters constituting said combined promoter have the same directional property and the P_L promoter is located upstream of said DNA sequence so as to have the directional property which permits transcription of said DNA sequence.

2. The recombinant plasmid of claim 1 wherein said L-phenylalanine ammonia-lyase has the following amino acid sequence:

| 1 | | | | | | | | | 10 |
|---|---|---|---|---|---|---|---|---|---|
| Met | Ala | Pro | Ser | Leu | Asp | Ser | Ile | Ser | His |
| 11 | | | | | | | | | 20 |
| Ser | Phe | Ala | Asn | Gly | Val | Ala | Ser | Ala | Lys |
| 21 | | | | | | | | | 30 |
| Gln | Ala | Val | Asn | Gly | Ala | Ser | Thr | Asn | Leu |
| 31 | | | | | | | | | 40 |
| Ala | Val | Ala | Gly | Ser | His | Leu | Pro | Thr | Thr |
| 41 | | | | | | | | | 50 |
| Gln | Val | Thr | Gln | Val | Asp | Ile | Val | Glu | Lys |
| 51 | | | | | | | | | 60 |
| Met | Leu | Ala | Ala | Pro | Thr | Asp | Ser | Thr | Leu |
| 61 | | | | | | | | | 70 |
| Glu | Leu | Asp | Gly | Tyr | Ser | Leu | Asn | Leu | Gly |
| 71 | | | | | | | | | 80 |
| Asp | Val | Val | Ser | Ala | Ala | Arg | Lys | Gly | Arg |
| 81 | | | | | | | | | 90 |
| Pro | Val | Arg | Val | Lys | Asp | Ser | Asp | Glu | Ile |
| 91 | | | | | | | | | 100 |
| Arg | Ser | Lys | Ile | Asp | Lys | Ser | Val | Glu | Phe |
| 101 | | | | | | | | | 110 |
| Leu | Arg | Ser | Gln | Leu | Ser | Met | Ser | Val | Tyr |
| 111 | | | | | | | | | 120 |
| Gly | Val | Thr | Thr | Gly | Phe | Gly | Gly | Ser | Ala |
| 121 | | | | | | | | | 130 |
| Asp | Thr | Arg | Thr | Glu | Asp | Ala | Ile | Ser | Leu |
| 131 | | | | | | | | | 140 |
| Gln | Lys | Ala | Leu | Leu | Glu | His | Gln | Leu | Cys |
| 141 | | | | | | | | | 150 |
| Gly | Val | Leu | Pro | Ser | Ser | Phe | Asp | Ser | Phe |
| 151 | | | | | | | | | 160 |
| Arg | Leu | Gly | Arg | Gly | Leu | Glu | Asn | Ser | Leu |
| 161 | | | | | | | | | 170 |
| Pro | Leu | Glu | Val | Val | Arg | Gly | Ala | Met | Thr |
| 171 | | | | | | | | | 180 |
| Ile | Arg | Val | Asn | Ser | Leu | Thr | Arg | Gly | His |
| 181 | | | | | | | | | 190 |
| Ser | Ala | Val | Arg | Leu | Val | Val | Leu | Glu | Ala |
| 191 | | | | | | | | | 200 |
| Leu | Thr | Asn | Phe | Leu | Asn | His | Gly | Ile | Thr |
| 201 | | | | | | | | | 210 |
| Pro | Ile | Val | Pro | Leu | Arg | Gly | Thr | Ile | Ser |
| 211 | | | | | | | | | 220 |
| Ala | Ser | Gly | Asp | Leu | Ser | Pro | Leu | Ser | Tyr |
| 221 | | | | | | | | | 230 |
| Ile | Ala | Ala | Ala | Ile | Ser | Gly | His | Pro | Asp |
| 231 | | | | | | | | | 240 |
| Ser | Lys | Val | His | Val | Val | His | Glu | Gly | Lys |
| 241 | | | | | | | | | 250 |
| Glu | Lys | Ile | Leu | Tyr | Ala | Arg | Glu | Ala | Met |
| 251 | | | | | | | | | 260 |
| Ala | Leu | Phe | Asn | Leu | Glu | Pro | Val | Val | Leu |
| 261 | | | | | | | | | 270 |
| Gly | Pro | Lys | Glu | Gly | Leu | Gly | Leu | Val | Asn |
| 271 | | | | | | | | | 280 |
| Gly | Thr | Ala | Val | Ser | Ala | Ser | Met | Ala | Thr |
| 281 | | | | | | | | | 290 |
| Leu | Ala | Leu | His | Asp | Ala | His | Met | Leu | Ser |
| 291 | | | | | | | | | 300 |
| Leu | Leu | Ser | Gln | Ser | Leu | Thr | Ala | Met | Thr |
| 301 | | | | | | | | | 310 |
| Val | Glu | Ala | Met | Val | Gly | His | Ala | Gly | Ser |
| 311 | | | | | | | | | 320 |
| Phe | His | Pro | Phe | Leu | His | Asp | Val | Thr | Arg |
| 321 | | | | | | | | | 330 |
| Pro | His | Pro | Thr | Gln | Ile | Glu | Val | Ala | Gly |
| 331 | | | | | | | | | 340 |
| Asn | Ile | Arg | Lys | Leu | Leu | Glu | Gly | Ser | Arg |
| 341 | | | | | | | | | 350 |
| Phe | Ala | Val | His | His | Glu | Glu | Glu | Val | Lys |
| 351 | | | | | | | | | 360 |
| Val | Lys | Asp | Asp | Glu | Gly | Ile | Leu | Arg | Gln |
| 361 | | | | | | | | | 370 |
| Asp | Arg | Tyr | Pro | Leu | Arg | Thr | Ser | Pro | Gln |
| 371 | | | | | | | | | 380 |
| Trp | Leu | Gly | Pro | Leu | Val | Ser | Asp | Leu | Ile |
| 381 | | | | | | | | | 390 |
| His | Ala | His | Ala | Val | Leu | Thr | Ile | Glu | Ala |
| 391 | | | | | | | | | 400 |
| Gly | Gln | Ser | Thr | Thr | Asp | Asn | Pro | Leu | Ile |
| 401 | | | | | | | | | 410 |
| Asp | Val | Glu | Asn | Lys | Thr | Ser | His | His | Gly |
| 411 | | | | | | | | | 420 |
| Gly | Asn | Phe | Gln | Ala | Ala | Ala | Val | Ala | Asn |
| 421 | | | | | | | | | 430 |
| Thr | Met | Glu | Lys | Thr | Arg | Leu | Gly | Leu | Ala |
| 431 | | | | | | | | | 440 |
| Gln | Ile | Gly | Lys | Leu | Asn | Phe | Thr | Gln | Leu |
| 441 | | | | | | | | | 450 |
| Thr | Glu | Met | Leu | Asn | Ala | Gly | Met | Asn | Arg |
| 451 | | | | | | | | | 460 |
| Gly | Leu | Pro | Ser | Cys | Leu | Ala | Ala | Glu | Asp |
| 461 | | | | | | | | | 470 |
| Pro | Ser | Leu | Ser | Tyr | His | Cys | Lys | Gly | Leu |
| 471 | | | | | | | | | 480 |
| Asp | Ile | Ala | Ala | Ala | Ala | Tyr | Thr | Ser | Glu |
| 481 | | | | | | | | | 490 |
| Leu | Gly | His | Leu | Ala | Asn | Pro | Val | Thr | Thr |
| 491 | | | | | | | | | 500 |
| His | Val | Gln | Pro | Ala | Glu | Met | Ala | Asn | Gln |
| 501 | | | | | | | | | 510 |
| Ala | Val | Asn | Ser | Leu | Ala | Leu | Ile | Ser | Ala |
| 511 | | | | | | | | | 520 |
| Arg | Arg | Thr | Thr | Glu | Ser | Asn | Asp | Val | Leu |
| 521 | | | | | | | | | 530 |
| Ser | Leu | Leu | Leu | Ala | Thr | His | Leu | Tyr | Cys |
| 531 | | | | | | | | | 540 |
| Val | Leu | Gln | Ala | Ile | Asp | Leu | Arg | Ala | Ile |
| 541 | | | | | | | | | 550 |
| Glu | Phe | Glu | Phe | Lys | Lys | Gln | Phe | Gly | Pro |
| 551 | | | | | | | | | 560 |
| Ala | Ile | Val | Ser | Leu | Ile | Asp | Gln | His | Phe |
| 561 | | | | | | | | | 570 |
| Gly | Ser | Ala | Met | Thr | Gly | Ser | Asn | Leu | Arg |
| 571 | | | | | | | | | 580 |
| Asp | Glu | Leu | Val | Glu | Lys | Val | Asn | Lys | Thr |
| 581 | | | | | | | | | 590 |
| Leu | Ala | Lys | Arg | Leu | Glu | Gln | Thr | Asn | Ser |
| 591 | | | | | | | | | 600 |
| Tyr | Asp | Leu | Val | Pro | Arg | Trp | His | Asp | Ala |
| 601 | | | | | | | | | 610 |
| Phe | Ser | Phe | Ala | Ala | Gly | Thr | Val | Val | Glu |
| 611 | | | | | | | | | 620 |
| Val | Leu | Ser | Ser | Thr | Ser | Leu | Ser | Leu | Ala |
| 621 | | | | | | | | | 630 |
| Ala | Val | Asn | Ala | Trp | Lys | Val | Ala | Ala | Ala |
| 631 | | | | | | | | | 640 |
| Glu | Ser | Ala | Ile | Ser | Leu | Thr | Arg | Gln | Val |
| 641 | | | | | | | | | 650 |
| Arg | Glu | Thr | Phe | Trp | Ser | Ala | Ala | Ser | Thr |
| 651 | | | | | | | | | 660 |
| Ser | Ser | Pro | Ala | Leu | Ser | Tyr | Leu | Ser | Pro |
| 661 | | | | | | | | | 670 |
| Arg | Thr | Gln | Ile | Leu | Tyr | Ala | Phe | Val | Arg |
| 671 | | | | | | | | | 680 |
| Glu | Glu | Leu | Gly | Val | Lys | Ala | Arg | Arg | Gly |
| 681 | | | | | | | | | 690 |
| Asp | Val | Phe | Leu | Gly | Lys | Gln | Glu | Val | Thr |
| 691 | | | | | | | | | 700 |
| Ile | Gly | Ser | Asn | Val | Ser | Lys | Ile | Tyr | Glu |
| 701 | | | | | | | | | 710 |
| Ala | Ile | Lys | Ser | Gly | Arg | Ile | Asn | Asn | Val |
| 711 | | | | | 716 | | | | |
| Leu | Leu | Lys | Met | Leu | Ala | | | | |

3. A strain of *Escherichia coli* which has been transformed with the recombinant plasmid of claim 2.

* * * * *